US012742191B2

(12) United States Patent
Deng et al.

(10) Patent No.: US 12,742,191 B2
(45) Date of Patent: Sep. 22, 2026

(54) METHOD FOR EXTRACTION AND MULTI-SCENARIO UTILIZATION OF FLAXSEED PROTEIN-POLYSACCHARIDE NATURAL MIXTURE

(71) Applicant: OIL CROPS RESEARCH INSTITUTE, CHINESE ACADEMY OF AGRICULTURAL SCIENCES, Wuhan (CN)

(72) Inventors: Qianchun Deng, Wuhan (CN); Dengfeng Peng, Wuhan (CN); Kangyu Li, Wuhan (CN); Jiaqi Shao, Wuhan (CN); Jieting Ye, Wuhan (CN)

(73) Assignee: OIL CROPS RESEARCH INSTITUTE, CHINESE ACADEMY OF AGRICULTURAL SCIENCES, Wuhan (CN)

( * ) Notice: Subject to any disclaimer, the term of this patent is extended or adjusted under 35 U.S.C. 154(b) by 516 days.

(21) Appl. No.: 18/459,401

(22) Filed: Aug. 31, 2023

(65) Prior Publication Data

US 2024/0117397 A1 Apr. 11, 2024

Related U.S. Application Data

(63) Continuation of application No. PCT/CN2023/091960, filed on May 4, 2023.

(30) Foreign Application Priority Data

Sep. 30, 2022 (CN) ........................ 202211212168.X

(51) Int. Cl.
*C12P 19/04* (2006.01)
*A23J 1/14* (2006.01)
(Continued)

(52) U.S. Cl.
CPC ............... *C12P 19/04* (2013.01); *A23J 1/146* (2013.01); *A23J 1/148* (2013.01); *A23L 2/38* (2013.01); *A23L 2/66* (2013.01)

(58) Field of Classification Search
CPC . C12P 19/04; A23J 1/146; A23J 1/148; A23L 2/38; A23L 2/66
(Continued)

(56) References Cited

U.S. PATENT DOCUMENTS

2008/0009606 A1 1/2008 Nakamura et al.
2015/0272190 A1 10/2015 Dake et al.
2022/0232852 A1* 7/2022 Pasternak ................ A23L 5/13

FOREIGN PATENT DOCUMENTS

CN 103030705 A 4/2013
CN 105037573 A 11/2015
(Continued)

OTHER PUBLICATIONS

International Search Report issued in corresponding International application No. PCT/CN2023/091960, mailed Aug. 22, 2023 (8 pages).
(Continued)

*Primary Examiner* — Brent T O'Hern

(57) ABSTRACT

A method for extraction and multi-scenario utilization of flaxseed protein-polysaccharide natural mixture includes: (1) crushing, sieving and degreasing flaxseed meal to obtain flaxseed degreased meal powder, and dissolving and stirring to obtain a flaxseed-meal-powder rinsing solution; (2) performing ultrasonic treatment or microwave treatment on the flaxseed-meal-powder rinsing solution, or adding bio-enzyme into the flaxseed-meal-powder rinsing solution and stirring in a water bath, and then centrifuging to obtain a supernatant and a precipitate and freeze-drying the supernatant to obtain mixture I; (3) using the mixture I to prepare powdered oil containing n-3 polyunsaturated fatty acid,
(Continued)

high-stability gel foam, or low-turbidity plant protein drink; (4) redissolving the precipitate obtained in (2), adjusting pH, magnetically stirring, ultrasonically treating, centrifuging, and freeze-drying a supernatant to obtain mixture II; and (5) using the mixture II to prepare low oil phase nanoemulsion, foamed emulsion, or meal replacement milkshake.

9 Claims, 8 Drawing Sheets

(51) Int. Cl.
*A23L 2/38* (2021.01)
*A23L 2/66* (2006.01)

(58) Field of Classification Search
USPC .......................................................... 426/656
See application file for complete search history.

(56) References Cited

FOREIGN PATENT DOCUMENTS

| | | | |
|---|---|---|---|
| CN | 108070630 | A | 5/2018 |
| CN | 108892705 | A | 11/2018 |
| CN | 110679915 | A | 1/2020 |
| CN | 111903981 | A | 11/2020 |
| CN | 114891062 | A | 8/2022 |
| CN | 115553374 | A | 1/2023 |

OTHER PUBLICATIONS

Written Opinion of the International Search Authority in corresponding International application No. PCT/CN2023/091960, mailed Aug. 22, 2023 (9 pages).
Notification to Grant Patent Right for Invention, Chinese Application No. 202211212168.X, mailed Mar. 30, 2023 (3 pages).
CNIPA, Office Action issued for Chinese Application No. 202211212168.X, mailed Mar. 9, 2023 (12 pages).
Xiaoye Hua et al., Research techniques and methods of environmental engineering microbiology, p. 40, issue date Jan. 31, 2020.
Jieru Feng et al., "Bulletin of Fermentation Science and Technology", Advances in protein-polysaccharide interaction at oil-water interface of emulsion, vol. 48, Issue 01, pp. 14-18, issue date Mar. 25, 2019.
Hongjie Li et al., "Journal of the Chinese Cereals and Oils Association", Effect of Restricted Enzymatic Hydrolysis on Functional Properties and Structure of Flaxseed Protein and Its Application in Ice Cream, vol. 36, Issue 12, pp. 34-43, issue date Mar. 25, 2019.
Lanxue Ma et al., "Journal of Food Safety and Quality", Functional properties of flaxseed gum and its application in food, vol. 12, Issue 7, pp. 2722-2727, issue date Apr. 15, 2021.
Ying Bai et al., "Food Science and Technology", Extraction and Physical Properties of Flaxseed Gum, vol. 45, Issue 11, pp. 217-223, issue date Nov. 20, 2020.
Pratibha Kaushik et al., "Food Research International", Complex coacervation between flaxseed protein isolate and flaxseed gum, vol. 72, pp. 91-97, issue date Apr. 1, 2015.
Lingli Ouyang et al., "Chinese oils", Enzymatic degumming process of flaxseed cake, vol. 42, Issue 05, pp. 127-131, issue date May 20, 2017.
Mengjia Sun et al., "Food Hydrocolloids", Reducing off-flavors in plant-based omega-3 oil emulsions using interfacial engineering: Coating algae oil droplets with pea protein/flaxseed gum, vol. 122, pp. 1-14, issue date Jul. 28, 2021.
Xiaofeng Li et al., "Journal of the Chinese Cereals and Oils Association", Comparison of Microwave Assisted Extraction Methods and Hot Water Extraction on Flaxseed Gum Extraction, vol. 31, Issue 08, pp. 55-61, issue date Aug. 25, 2016.
Aijuan Feng et al., "Food Research and Development", Study on Extraction of Flaxseed Gums from Flaxseed by Ultrasonic Technique, vol. 37, Issue 10, pp. 66-69, issue date May 20, 2016.
Tingting Liu et al., "China Oils and Fats", Advances in nutrients extraction, functions and applications of flaxseed, vol. 45, Issue 03, pp. 90-97, issue date Mar. 20, 2020.
Weiwei Cao et al., "Food Research and Development", Research Progress in the Utilization of Flaxseed Meal Food, vol. 38, Issue 07, pp. 200-205, issue date Apr. 10, 2017.

* cited by examiner

METHOD FOR EXTRACTION AND MULTI-SCENARIO UTILIZATION OF FLAXSEED PROTEIN-POLYSACCHARIDE NATURAL MIXTURE

TECHNICAL FIELD

The present invention relates to protein extraction technique and multi-scenario application, particularly to a method for extraction and multi-scenario utilization of a flaxseed protein-polysaccharide natural mixture.

BACKGROUND

Protein is one of three nutrients required by the human body, and its good functional properties (such as gelation property, as well as foaming and emulsifying properties) can give good texture and taste for food. Therefore, protein is widely used in the food industry. However, if protein is used separately, product instability is caused around its isoelectric point, and the protein forms aggregates at this time, leading to the decrease of solubility.

Polysaccharide has processing characteristics and rheological properties that other substances do not have. It plays an important role in the food ingredient industry, and mainly serves as a stabilizer and a thickener. For example, polysaccharide is added to drinks, which can increase the viscosity and stability. However, the emulsifying and foaming properties of the individual polysaccharide are generally poor.

Many studies indicate that the artificial compounding of the protein and the polysaccharide is beneficial to improve the functional properties of the protein, so as to effectively solve the problems existing when the protein or the polysaccharide is used separately. The reason is that, on the one hand, the existence of the polysaccharide can complement the advantages of the protein to reflect the synergistic effect on functional properties; and on the other hand, non-covalent interactions (such as electrostatic interactions, hydrophobic interactions, Van der Waals force, and hydrogen bonds) in protein-polysaccharide systems drive non-covalent binding of the protein and the polysaccharide in the systems to achieve the effect of improving the functional properties, which cannot be achieved by the protein or polysaccharide alone. Based on this, the concept of simultaneously extracting and applying protein-polysaccharide mixture from biomass emerges.

Flaxseed yield is abundant in China, and flaxseed meal contains a lot of protein and polysaccharide. Relevant literature shows that the protein content of degreased flaxseed meal is 35-45% and the total sugar content is 30-35%. The applicant actually measures that the protein content of the degreased flaxseed meal is 41.74±0.53% and the total sugar content is 31.58±1.02%. However, the flaxseed has special structure and contains abundant flaxseed gum on the surface, which makes it difficult to extract flaxseed protein. At present, the traditional technique mainly uses alkali-solution and acid-isolation method to extract the flaxseed protein. For example, CN 114287507 A, a key process method based on comprehensive extraction of flaxseed core components; CN 108902441 A, a deep processing method of flaxseed meal; CN 108325581 A, a comprehensive utilization process of flaxseed; "optimization of flaxseed oil protein separation process based on alkali-solution and acid-isolation", Wenlai Hao, Contemporary Chemical Industry, Volume 48, Issue 10, October 2019, etc. However, because the above extraction techniques are oriented to obtain flaxseed protein concentrate or protein isolate, the step of degumming is required. Some studies indicate that the artificial compounding of the flaxseed gum and the protein can improve the functional properties, such as emulsifying properties. Therefore, it is not necessary to extract high-purity flaxseed protein or polysaccharide in industrial production, and flaxseed protein-polysaccharide natural mixtures shall be extracted in a milder way by using their natural advantages.

In addition, the applicant finds that the protein-polysaccharide natural mixtures can be extracted from the flaxseed meal by the conventional water extraction method, and have good emulsifying properties foaming capacity and solubility. Compared with the extraction of high-purity flaxseed protein, the process is simpler and milder in steps, and the application range is expanded based on the special properties of flaxseed polysaccharide. However, the extraction technique mainly has two disadvantages. One disadvantage is low extraction rate, and the other is poor orientability for the extract, and the application scenario is limited.

Therefore, the problem to be solved urgently by those skilled in the art is how to realize the efficient extraction and multi-scenario utilization of the flaxseed protein-polysaccharide natural mixtures.

SUMMARY

In view of this, the purpose of the present invention is to provide a method for extraction and multi-scenario utilization of a flaxseed protein-polysaccharide natural mixture, to realize the efficient extraction and multi-scenario utilization of a co-extracted flaxseed protein-polysaccharide mixture.

To achieve the above purpose, the present invention adopts the following technical solution:

A method for extraction and multi-scenario utilization of a flaxseed protein-polysaccharide natural mixture specifically comprises the following steps:

(1) raw material pretreatment firstly crushing, sieving, and degreasing flaxseed meal to obtain flaxseed degreased meal powder; and then dissolving the flaxseed degreased meal in water and stirring to obtain flaxseed degreased meal rinsing solution;

(2) extraction of flaxseed protein-polysaccharide natural mixture I firstly conducting ultrasonic treatment for the flaxseed degreased meal rinsing solution, or firstly conducting microwave treatment for the flaxseed degreased meal rinsing solution, or firstly adding bio-enzyme into the flaxseed degreased meal rinsing solution and stirring in a water bath; then centrifuging, taking supernatant and freeze-drying to obtain the flaxseed protein-polysaccharide natural mixture I;

(3) utilization of flaxseed protein-polysaccharide natural mixture I firstly, dissolving the flaxseed protein-polysaccharide natural mixture I, gum Arabic, and maltodextrin in water and hydrated overnight; then adding oil rich in n-3 polyunsaturated fatty acid, shearing, introducing a high-pressure microfluidization, adding food grade silica powder and shaking up to obtain emulsion rich in n-3 polyunsaturated fatty acid; and finally, spray-drying the emulsion to obtain powdered oil rich in n-3 polyunsaturated fatty acid;

or, firstly dissolving the flaxseed protein-polysaccharide natural mixture I in water and adjusting pH to acidity; then heating in the water bath and whipping; and finally, treating in an ice bath to room temperature to obtain high-stability gel foam;

or, using the flaxseed protein-polysaccharide natural mixture I as a highly soluble protein ingredient for preparing a low-turbidity plant protein drink;

(4) extraction of flaxseed protein-polysaccharide natural mixture II firstly, redissolving the precipitate obtained after centrifugation in step (2) to the same volume as the flaxseed degreased meal rinsing solution, adjusting the pH to alkalinity and conducting magnetic stirring to obtain the alkali extraction solution of the flaxseed degreased meal; then, conducting ultrasonic treatment for the alkali extraction solution of the flaxseed degreased meal, centrifuging, taking supernatant and freeze-drying to obtain the flaxseed protein-polysaccharide natural mixture II;

(5) utilization of flaxseed protein-polysaccharide natural mixture II firstly dissolving the flaxseed protein-polysaccharide natural mixture II in water, then adding the oil rich in n-3 polyunsaturated fatty acid, and after shearing, introducing the high-pressure microfluidization to obtain low oil phase nano-emulsion;

or, firstly dissolving the flaxseed protein-polysaccharide natural mixture II and sucrose in water, adding coconut oil, shearing to obtain macroemulsion, introducing the high-pressure microfluidization to obtain miniemulsion, then adding the flaxseed protein-polysaccharide natural mixture I for magnetic stirring, aging, adjusting pH to acidity, and whipping in an ice bath to obtain foamed emulsion;

or, mixing and crushing the flaxseed protein-polysaccharide natural mixture II, pea protein isolate, hempseed protein, soybean protein isolate, perilla protein, perilla peptide, microcapsule powder rich in n-3 polyunsaturated fatty acid, medium chain triglycerides microcapsule powder, psyllium husk powder, maltodextrin, oat flour, flaxseed powder, resistant dextrin, chitosan oligosaccharide, yacon, inulin, fructo oligosaccharide, erythritol, konjak flour, and stevioside to obtain a meal replacement milkshake.

The present invention has the following beneficial effects:

Compared with the traditional extraction mode (such as alkali-solution and acid-isolation method) of flaxseed protein, the method of the present invention can enrich the flaxseed protein more efficiently, greenly and mildly, and the method can extract polysaccharide from flaxseed meal to form the flaxseed protein-polysaccharide natural mixture. Physical field/bio-enzyme coupling ultrasonic technique solves the bottleneck problem of low extraction rate of the flaxseed protein-polysaccharide natural mixture from water extraction. By controlling the types of physical field/enzyme, operating parameters, and treatment time, flaxseed protein-polysaccharide natural mixtures of different proportions can be acquired targeted and endowed with multiple functional properties, so as to satisfy the multi-scenario utilization of mixtures I and II.

The action mechanism of the present invention is as follows:

The present invention has three treatment modes for the flaxseed protein-polysaccharide natural mixture I, i.e., ultrasonic, microwave, and bio-enzyme. Unlike auxiliary protein extraction, due to the presence of polysaccharide such as flaxseed gum, the effects of the treatment modes on the native components of the flaxseed and the viscosity of the water extract must be considered.

Wherein:

1. Ultrasonic mainly uses the mechanical effects and the cavitation (such as microscopic and macroscopic flows, and high shear effects of shock wave and water jet), which achieves the effects of affecting protein structure, destroying cellular and subcellular structures to promote the dissolution of contents, decomposing the flaxseed gum into small molecular polysaccharides, and reducing the viscosity of water extract.

2. Microwave uses the synergy of thermal effect and non-thermal effect. Wherein the main mechanism of the thermal effect is that microwave can penetrate through the organic carbon chain as a whole, and the energy can quickly reach the functional groups of the extract, so as to promote the cell rupture, and achieve the property of thinning by heating for the flaxseed gum. The main mechanism of the non-thermal effect is that molecules are polarized under the action of a microwave electromagnetic field, and do polarity inversion motion to generate bond vibration, tearing and mutual friction and collision between particles, so as to promote the cell rupture, so that the contents overflow and diffuse into the solvent.

3. The bio-enzyme mainly conducts enzymatic hydrolysis for the components in the cell wall of the native structure to promote the dissolution of contents, or decomposes macromolecular polysaccharides into micromolecules to play the role of reducing viscosity.

The treatment mode for the flaxseed protein-polysaccharide natural mixture II in the present invention is ultrasonic. In the process of ultrasonic treatment, the ultrasonic cavitation increases the surface area of solid-liquid contact; a large number of hole bubbles form high intensity of pressure around the protein particles, to promote the expansion of the protein structure, peptide bond fracture and exposure of hydrophilic amino acid, so that the protein solubility is changed and the rheological properties of the flaxseed protein-polysaccharide natural mixture II are also changed to a large extent.

In conclusion, the technical commonalities of the three means of the present invention are destroying of cell binding and reducing the viscosity of the extracting solution, so as to directionally acquire flaxseed protein and polysaccharide. Based on this, the increase of the extraction rate and multi-scenario application of the flaxseed protein-polysaccharide natural mixture can be realized.

Further, in above step (1), the sieve mesh number for sieving is 60 meshes; the volume ratio of the flaxseed degreased meal to the water is 1:15; and the rotational speed of the stirring is 1600 rpm, temperature is 40° C., and time is 3 h.

Further, in above step (2), the power of the ultrasonic treatment is 1-20 W/mL and time is 10-60 min; the temperature of the microwave treatment is 60° C., power is 40-100 W and time is 3-40 min; the bio-enzyme is pectase, cellulase or hemicellulase; the mass-to-volume ratio of the bio-enzyme to the flaxseed degreased meal rinsing solution is 1 g:100 mL; the temperature of the stirring in the water bath is 50° C., and time is 2 h; and the temperature of the centrifuging is 20° C., rotational speed is 10000 rpm and time is 30 min.

The above further technical solution has the beneficial effect that ultrasonic treatment improves the solubility and emulsifying properties of the sample and thus can be used as an emulsifier of cold water dispersible powdered oil. Because microwave treatment improves the foaming capacity of the sample, the component can be used as a high efficiency foaming agent in pure plant-based cake. Because bio-enzyme treatment greatly improves the solubility of the sample, the component can be used as the ingredient of plant protein with high solubility to prepare low turbidity plant protein beverages.

Further, in above step (3), in the preparation process of the powdered oil, the mass-to-volume ratio of the flaxseed protein-polysaccharide natural mixture I, the gum Arabic, the maltodextrin, the water, the oil rich in n-3 polyunsaturated fatty acid and the food grade silica powder is 2.5 g:2.5 g:5 g:100 mL:2.5 g:0.3 g; the temperature of hydrating overnight is 4° C.; the shear rate is 15000 rpm and time is 10 min; the pressure of the high-pressure microfluidization is 750 bar and cycle times is 3; the air inlet temperature of the spray drying is 160° C., and a feed rate is 7 mL/min.

Further, in above step (3), in the preparation process of the foam, the mass-to-volume ratio of the flaxseed protein-polysaccharide natural mixture I to the water is 2 g:50 mL; the pH is adjusted to 3.5; the temperature of the heating in the water bath is 50° C. and time is 10 min; and the whipped time is 5 min.

Further, in above step (4), the pH is adjusted to 9.0; the time of the magnetic stirring is 2 h; the power of the ultrasonic treatment is 1-20 W/mL and time is 10-60 min; and the temperature of the centrifuging is 4° C., the rotational speed is 10000 rpm and time is 30 min.

Further, in above step (5), in the preparation process of the nanoemulsion with low oil phase, the mass-to-volume ratio of the flaxseed protein-polysaccharide natural mixture II, the water and the oil rich in n-3 polyunsaturated fatty acid is 1.5 g:100 mL:3 g; the shear rate is 15000 rpm and time is 5 min; and the pressure of the high-pressure microfluidization is 500 bar and cycle times is 3.

The above further technical solution has the beneficial effects that because the two-step ultrasonic coupling improves the emulsifying stability of the sample, the component can be used as the emulsifier for preparing low oil phase nanoemulsion (<5%) and can be used in the preparation of complex plant milk in the future.

Further, in above step (5), in the preparation process of the foamed emulsion, the mass-to-volume ratio of the flaxseed protein-polysaccharide natural mixture II, the sucrose, the water, the coconut oil and the flaxseed protein-polysaccharide natural mixture I is 2 g:15 g:90 mL:10 mL:2 g; the temperature of the coconut oil is 60° C.; the shear rate is 15000 rpm and time is 5 min; the pressure of the high-pressure microfluidization is 500 bar and cycle times is 2; the time of the magnetic stirring is 6 h; the temperature of the aging is 4° C., and time is 6 h; the pH is adjusted to 4.0; and the time of the whipping is 20 min.

Further, in above step (5), in the preparation process of the meal replacement milkshake, the weight parts of the raw materials are as follow: 2 parts of the flaxseed protein-polysaccharide natural mixture II, 9 parts of the pea protein isolate, 3 parts of the hempseed protein, 7 parts of the soybean protein isolate, 5 parts of the perilla protein, 3 parts of the perilla peptide, 5 parts of the flaxseed oil microcapsule powder, 3 parts of the medium chain triglycerides microcapsule powder, 2 parts of the psyllium husk powder, 6 parts of the maltodextrin, 1 part of the oat flour, 1 part of the flaxseed powder, 5 parts of the resistant dextrin, 0.1 part of the chitosan oligosaccharide, 0.5 part of the yacon, 1 part of the inulin, 1 part of the fructo oligosaccharide, 1 part of the erythritol, 2 parts of the konjaku flour, and 0.04 part of the stevioside.

The above further technical solution has the beneficial effects that ultrasonic treatment increases the extraction rate of the sample and the total content of protein and polysaccharide, so the component can be added as a nutritional supplement to the meal replacement milkshake.

It can be known from the above technical solution that compared with the existing technique, the present invention has the following beneficial effects:

1. The traditional protein extraction mode is oriented to obtain protein concentrate or protein isolate. It is complex in technique and high in energy consumption, needs the intervention of strong acid and alkali environments or organic solvents, and is not green or environment-friendly. The co-extraction technique of the present invention is oriented towards functional properties and multi-scenario application, and is green and moderate, simple in technique, efficient and environment-friendly.

2. In terms of operation, the present invention does not need degumming, and is simple in technique; in terms of pH, the present invention is mild in reaction conditions; and in terms of solid-liquid ratio, the present invention is more energy-saving.

3. Compared with the traditional extraction mode of flaxseed protein, the method of the present invention can extract active components from the flaxseed meal more efficiently, greenly and moderately. The method solves the problem of low extraction rate of the flaxseed protein-polysaccharide natural mixture from water extraction, and can obtain flaxseed protein-polysaccharide natural mixtures of different proportions. The method enriches the orientability of the extraction process and can realize the multi-scenario utilization of different components.

DETAILED DESCRIPTION

The technical solutions in embodiments of the present invention will be clearly and fully described below. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

In the following embodiments, the variety of flaxseed is flaxseed yellow seed Zhangya 2#.

Embodiment 1

Figure 1:
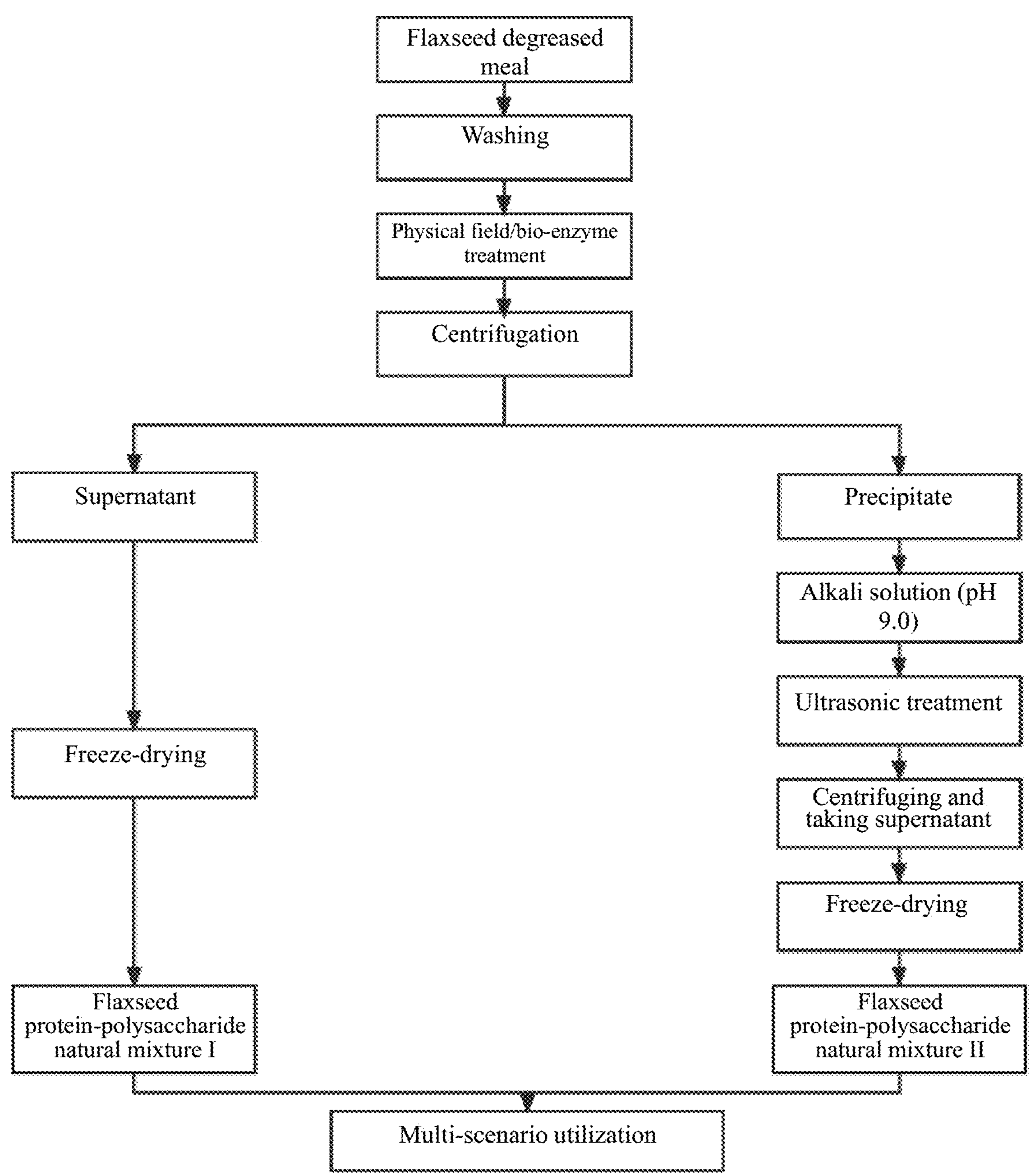
FIG. 1 is a flow chart of a method for extraction and multi-scenario utilization of flaxseed protein-polysaccharide natural mixture in embodiments 1-27.

A method for extraction and multi-scenario utilization of a flaxseed protein-polysaccharide natural mixture, as shown in FIG. 1, specifically comprises the following steps:

(1) raw material pretreatment firstly crushing flaxseed meal, then sieving by a 60-mesh sieve and degreasing to obtain flaxseed degreased meal powder; and then dissolving the flaxseed degreased meal in water at a volume ratio of 1:15 and stirring in a water bath of 40° C. at 1600 rpm for 3 h to obtain flaxseed degreased meal rinsing solution;

(2) extraction of flaxseed protein-polysaccharide natural mixture I firstly, conducting ultrasonic treatment for the flaxseed degreased meal rinsing solution by an ultrasonic cell crusher; setting ultrasonic power as 1 W/mL and ultrasonic time as 60 min; at the same time, to avoid solution overheating in the ultrasonic process, keeping solution temperature at 25° C. by an ice bath; then centrifuging at 10000 rpm at 20° C. for 30 min, taking supernatant and freeze-drying to obtain the flaxseed protein-polysaccharide natural mixture I;

(3) utilization of flaxseed protein-polysaccharide natural mixture I firstly, dissolving 2.5 g of flaxseed protein-polysaccharide natural mixture I, 2.5 g of gum Arabic and 5 g of maltodextrin in 100 mL of water and hydrating overnight at 4° C.;

then adding 2.5 g of flaxseed oil, shearing by a high-speed disperser for 10 min at 15000 rpm, then introducing a high-pressure microfluidization with a pressure of 750 bar for three cycles, adding 0.3 g of food grade silica powder and shaking up to obtain flaxseed oil emulsion; finally, introducing the flaxseed oil emulsion into a spray dryer for spray drying, setting air inlet temperature as 160° C. and a feed rate as 7 mL/min; and collecting products in a cyclone separator and a collector to obtain powdered oil;

(4) extraction of flaxseed protein-polysaccharide natural mixture II firstly, redissolving the precipitate obtained after centrifugation in step (2) to the same volume as the flaxseed degreased meal rinsing solution, adjusting the pH to 9.0 and conducting magnetic stirring for 2 h; because the pH of the solution is decreased with the dissolution of the substance, the pH is adjusted every 0.5 h in the magnetic stirring process, and the alkali extraction solution of the flaxseed degreased meal is obtained; then, conducting ultrasonic treatment for the alkali extraction solution of the flaxseed degreased meal by an ultrasonic cell crusher; setting ultrasonic power as 1 W/mL and ultrasonic time as 60 min; at the same time, to avoid solution overheating in the ultrasonic process, keeping solution temperature at 25° C. by an ice bath; finally centrifuging at 10000 rpm at 4° C. for 30 min, taking supernatant and freeze-drying to obtain the flaxseed protein-polysaccharide natural mixture II;

(5) utilization of flaxseed protein-polysaccharide natural mixture II firstly dissolving 1.5 g of flaxseed protein-polysaccharide natural mixture II in 100 mL of water, then adding 3 g of flaxseed oil, shearing by a high-speed disperser for 5 min at 15000 rpm, and then introducing a high-pressure microfluidization with a pressure of 500 bar for three cycles to obtain the nanoemulsion with low oil phase.

Embodiment 2

The differences from embodiment 1 are only that in step (1), the ultrasonic power is 1 W/mL and the ultrasonic time is 60 min, and in step (4), the ultrasonic power is 10 W/mL and the ultrasonic time is 30 min.

Embodiment 3

The differences from embodiment 1 are only that in step (1), the ultrasonic power is 1 W/mL and the ultrasonic time is 60 min, and in step (4), the ultrasonic power is 20 W/mL and the ultrasonic time is 10 min.

Embodiment 4

The differences from embodiment 1 are only that in step (1), the ultrasonic power is 10 W/mL and the ultrasonic time is 30 min, and in step (4), the ultrasonic power is 1 W/mL and the ultrasonic time is 60 min.

Embodiment 5

The differences from embodiment 1 are only that in step (1), the ultrasonic power is 10 W/mL and the ultrasonic time is 30 min, and in step (4), the ultrasonic power is 10 W/mL and the ultrasonic time is 30 min.

Embodiment 6

The differences from embodiment 1 are only that in step (1), the ultrasonic power is 10 W/mL and the ultrasonic time is 30 min, and in step (4), the ultrasonic power is 20 W/mL and the ultrasonic time is 10 min.

Embodiment 7

The differences from embodiment 1 are only that in step (1), the ultrasonic power is 20 W/mL and the ultrasonic time is 10 min, and in step (4), the ultrasonic power is 1 W/mL and the ultrasonic time is 60 min.

Embodiment 8

The differences from embodiment 1 are only that in step (1), the ultrasonic power is 20 W/mL and the ultrasonic time is 10 min, and in step (4), the ultrasonic power is 10 W/mL and the ultrasonic time is 30 min.

Embodiment 9

The differences from embodiment 1 are only that in step (1), the ultrasonic power is 20 W/mL and the ultrasonic time is 10 min, and in step (4), the ultrasonic power is 20 W/mL and the ultrasonic time is 10 min.

Embodiment 10

A method for extraction and multi-scenario utilization of a flaxseed protein-polysaccharide natural mixture, as shown in FIG. 1, specifically comprises the following steps:

(1) raw material pretreatment firstly crushing flaxseed meal, then sieving by a 60-mesh sieve and degreasing to obtain flaxseed degreased meal powder; and then dissolving the flaxseed degreased meal in water at a volume ratio of 1:15 and stirring at 1600 rpm for 3 h to obtain flaxseed degreased meal rinsing solution;

(2) extraction of flaxseed protein-polysaccharide natural mixture I firstly, conducting microwave treatment for the flaxseed degreased meal rinsing solution at temperature of 60° C., power of 40 W and time for 40 min; then, centrifuging at 10000 rpm at 20° C. for 30 min, taking supernatant and freeze-drying to obtain the flaxseed protein-polysaccharide natural mixture I;

(3) utilization of flaxseed protein-polysaccharide natural mixture I firstly dissolving 2 g of flaxseed protein-polysaccharide natural mixture I in 50 mL of water and adjusting pH to 3.5; then heating in a water bath at 50° C. for 10 min, and whipping the solution by a hand-held foam maker for 5 min; and finally, treating in an ice bath to room temperature to obtain high-stability gel foam;

(4) extraction of flaxseed protein-polysaccharide natural mixture II firstly, redissolving the precipitate obtained after centrifugation in step (2) to the same volume as the flaxseed degreased meal rinsing solution, adjusting the pH to 9.0 and conducting magnetic stirring for 2 h; because the pH of the solution is decreased with the dissolution of the substance, the pH is adjusted every 0.5 h in the magnetic stirring process, and the alkali extraction solution of the flaxseed degreased meal is obtained; then, conducting ultrasonic treatment for the alkali extraction solution of the flaxseed degreased meal; setting ultrasonic power as 1 W/mL and time as 60 min; at the same time, to avoid solution overheating in the ultrasonic process, keeping solution temperature at 25° C. by an ice bath; finally centrifuging at 10000 rpm at 4° C. for 30 min, taking supernatant and freeze-drying to obtain the flaxseed protein-polysaccharide natural mixture II;

(5) utilization of flaxseed protein-polysaccharide natural mixture II firstly dissolving 2 g of flaxseed protein-polysaccharide natural mixture II and 15 g of sucrose in 90 mL of water, adding 10 mL of coconut oil at 60° C., shearing by a high-speed disperser for 5 min at 15000 rpm to obtain macroemulsion, introducing a high-pressure microfluidization with pressure of 500 bar for 2 cycles to obtain miniemulsion, then adding 2 g of flaxseed protein-polysaccharide natural mixture I for magnetic stirring for 6 h, aging at 4° C. for 6 h, adjusting pH to 4.0, and whipping by the hand-held foam maker in an ice bath for 20 min to obtain foamed emulsion.

Embodiment 11

The differences from embodiment 10 are only that in step (1), the microwave power is 40 W/mL and the microwave time is 40 min, and in step (4), the ultrasonic power is 10 W/mL and the ultrasonic time is 30 min.

Embodiment 12

The differences from embodiment 10 are only that in step (1), the microwave power is 40 W/mL and the microwave time is 40 min, and in step (4), the ultrasonic power is 20 W/mL and the ultrasonic time is 10 min.

Embodiment 13

The differences from embodiment 10 are only that in step (1), the microwave power is 50 W/mL and the microwave time is 20 min, and in step (4), the ultrasonic power is 1 W/mL and the ultrasonic time is 60 min.

Embodiment 14

The differences from embodiment 10 are only that in step (1), the microwave power is 50 W/mL and the microwave time is 20 min, and in step (4), the ultrasonic power is 10 W/mL and the ultrasonic time is 30 min.

Embodiment 15

The differences from embodiment 10 are only that in step (1), the microwave power is 50 W/mL and the microwave time is 20 min, and in step (4), the ultrasonic power is 20 W/mL and the ultrasonic time is 10 min.

Embodiment 16

The differences from embodiment 10 are only that in step (1), the microwave power is 100 W/mL and the microwave time is 3 min, and in step (4), the ultrasonic power is 1 W/mL and the ultrasonic time is 60 min.

Embodiment 17

The differences from embodiment 10 are only that in step (1), the microwave power is 100 W/mL and the microwave time is 3 min, and in step (4), the ultrasonic power is 10 W/mL and the ultrasonic time is 30 min.

Embodiment 18

The differences from embodiment 10 are only that in step (1), the microwave power is 100 W/mL and the microwave time is 3 min, and in step (4), the ultrasonic power is 20 W/mL and the ultrasonic time is 10 min.

Embodiment 19

A method for extraction and multi-scenario utilization of a flaxseed protein-polysaccharide natural mixture, as shown in FIG. 1, specifically comprises the following steps:

(1) raw material pretreatment firstly crushing flaxseed meal, then sieving by a 60-mesh sieve and degreasing to obtain flaxseed degreased meal powder; and then dissolving the flaxseed degreased meal in water at a volume ratio of 1:15 and stirring at 1600 rpm for 3 h to obtain flaxseed degreased meal rinsing solution;

(2) extraction of flaxseed protein-polysaccharide natural mixture I firstly, adding 1 g of pectase to 100 mL of flaxseed degreased meal rinsing solution and stirring in a water bath at 50° C. for 2 h; then, centrifuging at 10000 rpm at 20° C. for 30 min, taking supernatant and freeze-drying to obtain the flaxseed protein-polysaccharide natural mixture I;

(3) utilization of flaxseed protein-polysaccharide natural mixture I using the flaxseed protein-polysaccharide natural mixture I as a highly soluble protein ingredient for preparing a low-turbidity plant protein drink;

(4) extraction of flaxseed protein-polysaccharide natural mixture II firstly, redissolving the precipitate obtained after centrifugation in step (2) to the same volume as the flaxseed degreased meal rinsing solution, adjusting the pH to 9.0 and conducting magnetic stirring for 2 h; because the pH of the solution is decreased with the dissolution of the substance, the pH is adjusted every 0.5 h in the magnetic stirring process, and the alkali extraction solution of the flaxseed degreased meal is obtained; then, conducting ultrasonic treatment for the alkali extraction solution of the flaxseed degreased meal; setting ultrasonic power as 1 W/mL and time as 60 min; at the same time, to avoid solution overheating in the ultrasonic process, keeping solution temperature at 25° C. by an ice bath; finally centrifuging at 10000 rpm at 4° C. for 30 min, taking supernatant and freeze-drying to obtain the flaxseed protein-polysaccharide natural mixture II;

(5) utilization of flaxseed protein-polysaccharide natural mixture II mixing and crushing 2 g of flaxseed protein-polysaccharide natural mixture II, 9 g of pea protein isolate, 3 g of hemp seed protein, 7 g of soybean protein isolate, 5 g of perilla protein, 3 g of perilla peptide, 5 g of flaxseed oil microcapsule powder, 3 g of medium chain triglycerides microcapsule powder, 2 g of psyllium husk powder, 6 g of maltodextrin, 1 g of oat flour, 1 g of flaxseed powder, 5 g of resistant dextrin, 0.1 g of chitosan oligosaccharide, 0.5 g of yacon, 1 g of inulin, 1 g of fructo oligosaccharide, 1 g of erythritol, 2 g of konjaku powder and 0.04 g of stevioside in a crusher to obtain a meal replacement milkshake.

Embodiment 20

The differences from embodiment 19 are only that in step (1), the bio-enzyme is pectase, and in step (4), the ultrasonic power is 10 W/mL and the ultrasonic time is 30 min.

Embodiment 21

The differences from embodiment 19 are only that in step (1), the bio-enzyme is pectase, and in step (4), the ultrasonic power is 20 W/mL and the ultrasonic time is 10 min.

Embodiment 22

The differences from embodiment 19 are only that in step (1), the bio-enzyme is cellulase, and in step (4), the ultrasonic power is 1 W/mL and the ultrasonic time is 60 min.

Embodiment 23

The differences from embodiment 19 are only that in step (1), the bio-enzyme is cellulase, and in step (4), the ultrasonic power is 10 W/mL and the ultrasonic time is 30 min.

Embodiment 24

The differences from embodiment 19 are only that in step (1), the bio-enzyme is cellulase, and in step (4), the ultrasonic power is 20 W/mL and the ultrasonic time is 10 min.

Embodiment 25

The differences from embodiment 19 are only that in step (1), the bio-enzyme is hemicellulase, and in step (4), the ultrasonic power is 1 W/mL and the ultrasonic time is 60 min.

Embodiment 26

The differences from embodiment 19 are only that in step (1), the bio-enzyme is hemicellulase, and in step (4), the ultrasonic power is 10 W/mL and the ultrasonic time is 30 min.

Embodiment 27

The differences from embodiment 19 are only that in step (1), the bio-enzyme is hemicellulase, and in step (4), the ultrasonic power is 20 W/mL and the ultrasonic time is 10 min.

Reference Example

Figure 2:
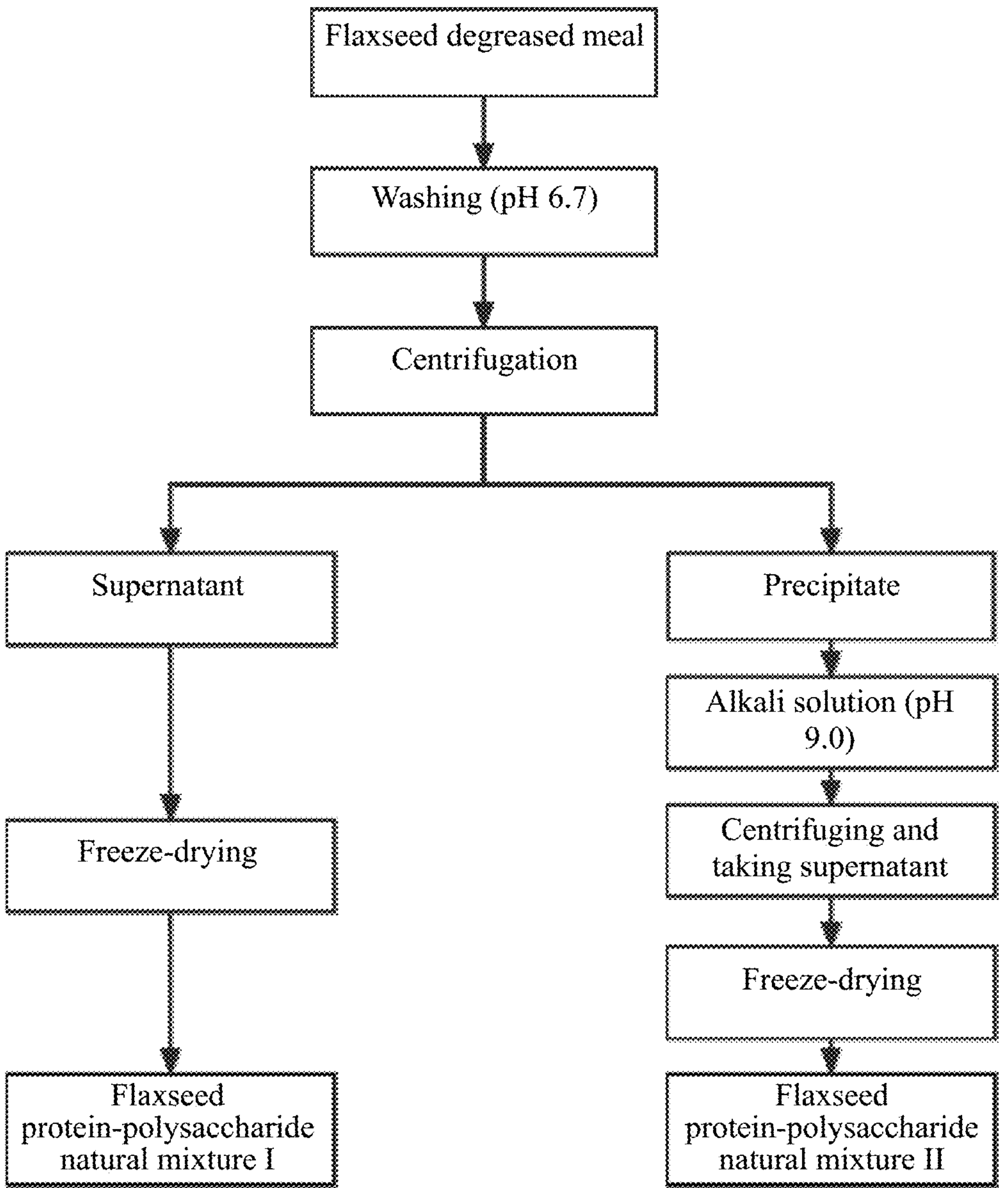
FIG. 2 is a flow chart of extraction of flaxseed protein-polysaccharide natural mixture without physical field/bio-enzyme coupling.

A method for extracting a flaxseed protein-polysaccharide natural mixture without physical field/bio-enzyme coupling, as shown in FIG. 2, specifically comprises the following steps:

(1) raw material pretreatment firstly crushing flaxseed meal, then sieving by a 60-mesh sieve and degreasing to obtain flaxseed degreased meal powder; and then dissolving the flaxseed degreased meal in water at a volume ratio of 1:15 and stirring in a water bath of 40° C. at 1600 rpm for 3 h to obtain flaxseed degreased meal rinsing solution;

(2) extraction of flaxseed protein-polysaccharide natural mixture I centrifuging at 10000 rpm at 20° C. for 30 min, taking supernatant and freeze-drying to obtain the flaxseed protein-polysaccharide natural mixture I;

(3) extraction of flaxseed protein-polysaccharide natural mixture II firstly, redissolving the precipitate obtained after centrifugation in step (2) to the same volume as the flaxseed degreased meal rinsing solution, adjusting the pH to 9.0 and conducting magnetic stirring for 2 h; because the pH of the solution is decreased with the dissolution of the substance, the pH is adjusted every 0.5 h in the magnetic stirring process, and the alkali extraction solution of the flaxseed degreased meal is obtained; and finally centrifuging at 10000 rpm at 4° C. for 30 min, taking supernatant and freeze-drying to obtain the flaxseed protein-polysaccharide natural mixture II.

Performance Test

In the following tests:

Detection of extraction rate: mass percentage of the flaxseed protein-polysaccharide natural mixture and the flaxseed degreased meal.

Detection of protein content: a micro Kjeldahl method is used. Refer to the national standard GB 5009.5-2010.

Detection of total sugar content: a phenol-sulfuric acid method is used. Refer to the national standard GB/T 15672-2009.

Detection of solubility: a centrifugal tube is weighed and 20 mL 2% (w/v) flaxseed protein-polysaccharide natural mixture solution is prepared with ultrapure water. The solution is stirred magnetically for 2 h until completely dissolved, and the pH is adjusted to 7.0. Then, the solution is centrifuged (7200 g, 10 min, 4° C.), the supernatant is dumped and the centrifugal tube and the precipitate are merged and dried to constant weight. The solubility is calculated.

Detection of emulsifying activity index and emulsifying stability index: 15 mL of 1% (w/v) protein solution is prepared with ultrapure water, and the pH is adjusted to 7.5 mL of medium chain triglycerides is added and homogenized for 2 min with a high speed shearing machine (13400 r/min). 50 μL of emulsion is quickly absorbed in the middle and diluted with 5 mL of 0.1% SDS (pH 7.0). SDS solution is used as blank reference, and the absorbance value of the diluted emulsion is determined at 500 nm. After standing for 10 min, the absorbance is determined again under the same conditions as above. The emulsifying activity index and the emulsifying stability index are calculated according to the following formulas:

$$\text{Emulsifying activity index}(m^2/g) = \frac{2 \times 2.303 \times A_0 \times N}{c \times \varphi \times L \times 10000};$$

$$\text{Emulsifying stability index} = \frac{A_0}{A_0 - A_{10}} \times t;$$

In the formulas: N-dilution factor; c-protein concentration (g/mL); co-volume fraction of the oil phase; L-cuvette optical path; Ao-absorbance value at 500 nm at 0 min; A/o-absorbance value at 500 nm at 10 min; and t represents standing time.

Detection of foaming capacity and foaming stability: 15 mL of 1% (w/v) protein solution is prepared with ultrapure water, and the pH is adjusted to 7.0. The protein solution is shear for 2 min with a high speed disperser (13600 rpm). The protein solution and foam are immediately poured into a measuring cylinder and the foam volume is read out. After standing for 30 min and 60 min, the foam volume is read out again. The calculation formulas of the foaming capacity and the foaming stability are as follows:

$$\text{Foaming capacity}(\%) = \frac{V_2}{15} \times 100;$$

$$\text{Foaming stability}(\%) = \frac{V_{60}}{V_2} \times 100;$$

In the formulas: $V_2$ is the foam volume at 2 min and $V_{60}$ is the foam volume at 60 min.

1. Test of Flaxseed Protein-Polysaccharide Natural Mixtures I in Embodiments 1, 4 And 7

The flaxseed protein-polysaccharide natural mixtures I prepared in step (2) of embodiments 1, 4 and 7 were recorded as sample 1-1, sample 1-2 and sample 1-3 respectively; and the sample without ultrasonic treatment was used as control and recorded as sample 1-0. The extraction rate, protein content, total sugar content, protein and total sugar content, solubility, emulsifying activity index, emulsifying stability index, foaming capacity and foaming stability were tested respectively, and the results were shown in Table 1.

TABLE 1

Test Results of Samples 1-0, 1-1, 1-2 and 1-3

| Test Item | Control Sample 1-0 | Embodiment 1 Sample 1-1 | Embodiment 4 Sample 1-2 | Embodiment 7 Sample 1-3 |
|---|---|---|---|---|
| Ultrasonic power (W/mL) in step (2) | 0 | 1 | 10 | 20 |
| Ultrasonic time (min) in step (2) | 0 | 60 | 30 | 10 |
| Extraction rate (%) | 24.48b ± 2.52 | 43.75a ± 0.78 | 44.05a ± 0.75 | 43.21a ± 0.78 |
| Protein content (%) | 44.23a ± 1.14 | 43.75a ± 0.78 | 44.05a ± 0.75 | 43.21a ± 0.78 |
| Total sugar content | 36.54c ± 0.25 | 41.96b ± 0.85 | 44.12a ± 0.51 | 40.32b ± 0.71 |
| Protein and total (%) sugar content (%) | 80.78c ± 1.34 | 85.71b ± 0.87 | 88.17a ± 0.74 | 83.53b ± 0.71 |
| Solubility (%) | 78.82c ± 0.62 | 86.32a ± 0.38 | 83.38b ± 0.55 | 86.85a ± 0.90 |
| Emulsifying activity index ($m^2$/g) | 7.22a ± 0.07 | 6.82c ± 0.19 | 6.72c ± 0.04 | 7.07b ± 0.12 |
| Emulsifying stability index (min) | 24.33c ± 0.63 | 34.25a ± 1.87 | 28.82b ± 0.25 | 32.07ab ± 2.86 |
| Foaming capacity (%) | 96.89c ± 2.74 | 122.22b ± 5.67 | 145.56a ± 7.93 | 119.33b ± 1.96 |
| Foaming stability (%) | 26.56c ± 0.60 | 45.48a ± 0.63 | 36.23b ± 5.99 | 49.34a ± 0.87 |

It can be seen in Table 1 that ultrasonic treatment in step (2) significantly improves the extraction rate, the total sugar content, the protein and total sugar content, the solubility, the emulsifying stability index, the foaming capacity and the foaming stability of sample 1-0. This is because ultrasonic wave effectively damages the cell structure of flaxseed, reduces the viscosity of the extract and thus increases the dissolution of polysaccharide.

Embodiment 4 is an optimum embodiment. The extraction rate, the emulsifying stability index and the solubility of the sample 1-2 prepared under this condition are increased by 79.94%, 18.45% and 5.79% respectively.

The test item demonstrates that ultrasonic treatment can effectively change the substance composition and functional properties of the flaxseed protein-polysaccharide natural mixture (extracted in step 1) to achieve directional extraction in different application scenarios. Based on the improvement of the emulsifying stability index and the solubility of the mixture by the test method, the powdered oil prepared by the component as an emulsifier is subsequently displayed, but the sample is not limited to the application scenario.

2. Test of Powdered Oil in Embodiment 4

The powdered oil prepared in step (3) of embodiment 4 was photographed. The results were shown in FIG. 3.

Figure 3:
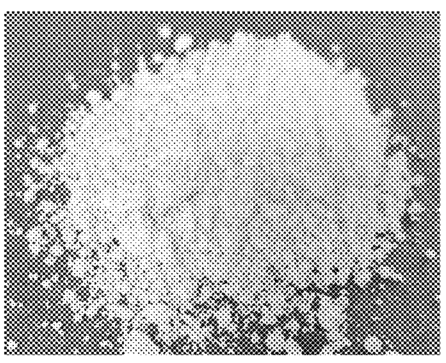
FIG. 3 shows powdered oil prepared in step (3) of embodiment 4.

It can be seen in FIG. 3 that the powdered oil has a white appearance and a light aroma of flaxseed, has no obvious oil leakage or caking phenomenon, and can be moistened in cold water.

3. Test of Flaxseed Protein-Polysaccharide Natural Mixtures ii in Embodiments 1-9

The flaxseed protein-polysaccharide natural mixtures II prepared in step (4) of embodiments 1-9 were recorded as sample 1-1-1, sample 1-1-2, sample 1-1-3, sample 1-2-1, sample 1-2-2, sample 1-2-3, sample 1-3-1, sample 1-3-2 and sample 1-3-3 respectively; and the samples without ultrasonic treatment were used as control and recorded as sample 1-1-0, sample 1-2-0 and sample 1-3-0 respectively. The extraction rate, protein content, total sugar content, protein and total sugar content, solubility, emulsifying activity index, emulsifying stability index, foaming capacity and foaming stability were tested respectively, and the results were shown in Tables 2-4.

TABLE 2

Test Results of Samples 1-1-0, 1-1-1, 1-1-2 and 1-1-3

| Test Item | Control Sample 1-1-0 | Embodiment 1 Sample 1-1-1 | Embodiment 2 Sample 1-1-2 | Embodiment 3 Sample 1-1-3 |
|---|---|---|---|---|
| Ultrasonic power (W/mL) in step (2) | 1 | | | |
| Ultrasonic time (min) in step (2) | 60 | | | |
| Ultrasonic power (W/mL) in step (4) | 0 | 1 | 10 | 20 |
| Ultrasonic time (min) in step (4) | 0 | 60 | 30 | 10 |
| Extraction rate (%) | 18.34b ± 0.17 | 26.13a ± 0.58 | 24.18a ± 0.68 | 23.89a ± 0.71 |
| Protein content (%) | 66.73c ± 0.43 | 71.58a ± 0.39 | 69.76b ± 0.83 | 69.30b ± 0.92 |
| Total sugar content (%) | 12.17a ± 0.68 | 10.11b ± 0.38 | 10.66b ± 0.35 | 10.46b ± 0.53 |
| Protein and total sugar content (%) | 78.90c ± 0.28 | 81.69a ± 0.27 | 80.42b ± 0.55 | 79.75b ± 0.80 |
| Solubility (%) | 82.72b ± 0.42 | 93.52a ± 1.73 | 95.64a ± 0.57 | 95.11a ± 0.93 |
| Emulsifying activity index ($m^2/g$) | 5.67d ± 0.07 | 7.81a ± 0.12 | 6.09c ± 0.05 | 6.87b ± 0.14 |
| Emulsifying stability index (min) | 26.84c ± 0.67 | 130.51a ± 15.75 | 112.13b ± 2.54 | 108.75b ± 7.58 |
| Foaming capacity (%) | 78.91d ± 1.42 | 94.00c ± 1.76 | 103.78b ± 1.68 | 112.00a ± 3.06 |
| Foaming stability (%) | 13.49a ± 0.71 | 11.83a ± 0.30 | 7.71b ± 0.07 | 7.13b ± 0.93 |

It can be seen in Table 2 that ultrasonic treatment in step (4) significantly improves the extraction rate, the protein content, the protein and total sugar content, the solubility, the emulsifying activity index, the emulsifying stability index and the foaming capacity of sample 1-1-0. This is because ultrasonic wave increases the dissolution of the protein.

TABLE 3

Test Results of Samples 1-2-0, 1-2-1, 1-2-2 and 1-2-3

| Test Item | Control Sample 1-2-0 | Embodiment 4 Sample 1-2-1 | Embodiment 5 Sample 1-2-2 | Embodiment 6 Sample 1-2-3 |
|---|---|---|---|---|
| Ultrasonic power (W/mL) in step (2) | 10 | | | |
| Ultrasonic time (min) in step (2) | 30 | | | |
| Ultrasonic power (W/mL) in step (4) | 0 | 1 | 10 | 20 |
| Ultrasonic time (min) in step (4) | 0 | 60 | 30 | 10 |
| Extraction rate (%) | 19.69b ± 0.79 | 26.01a ± 1.01 | 28.16a ± 0.86 | 25.33a ± 0.65 |
| Protein content (%) | 65.84b ± 2.10 | 74.67a ± 0.47 | 73.48a ± 0.79 | 73.05a ± 2.52 |
| Total sugar content (%) | 11.24c ± 0.72 | 12.39a ± 0.51 | 11.03b ± 0.34 | 10.83b ± 0.36 |
| Protein and total sugar content (%) | 77.08c ± 0.54 | 87.06a ± 0.61 | 84.51b ± 0.42 | 83.88a ± 0.31 |
| Solubility (%) | 88.32b ± 0.87 | 94.75a ± 0.82 | 95.39a ± 0.48 | 94.32a ± 1.13 |
| Emulsifying activity index ($m^2/g$) | 5.91c ± 0.03 | 6.41b ± 0.01 | 6.56b ± 0.10 | 8.06a ± 0.15 |
| Emulsifying stability index (min) | 45.50c ± 2.84 | 186.43a ± 54.80 | 126.33ab ± 32.88 | 109.81b ± 13.56 |
| Foaming capacity (%) | 88.44d ± 2.04 | 129.78b ± 4.29 | 122.89c ± 1.39 | 153.56a ± 2.34 |
| Foaming stability (%) | 25.34c ± 0.62 | 24.44a ± 0.45 | 26.55a ± 0.95 | 23.82b ± 5.01 |

It can be seen in Table 3 that ultrasonic treatment in step (4) significantly improves the extraction rate, the protein content, the protein and total sugar content, the solubility, the emulsifying activity index, the emulsifying stability index and the foaming capacity of sample 1-2-0. This is because ultrasonic wave increases the dissolution of the protein.

TABLE 4

Test Results of Samples 1-3-0, 1-3-1, 1-3-2 and 1-3-3

| Test Item | Control Sample 1-3-0 | Embodiment 7 Sample 1-3-1 | Embodiment 8 Sample 1-3-2 | Embodiment 9 Sample 1-3-3 |
|---|---|---|---|---|
| Ultrasonic power (W/mL) in step (2) | 20 | | | |
| Ultrasonic time (min) in step (2) | 10 | | | |
| Ultrasonic power (W/mL) in step (4) | 0 | 1 | 10 | 20 |
| Ultrasonic time (min) in step (4) | 0 | 60 | 30 | 10 |
| Extraction rate (%) | 20.16b ± 0.25 | 24.63a ± 0.87 | 27.94a ± 0.66 | 26.83a ± 0.54 |
| Protein content (%) | 67.39c ± 0.40 | 70.70b ± 0.50 | 72.03a ± 0.43 | 71.05b ± 0.44 |
| Total sugar content (%) | 10.35b ± 0.55 | 9.34b ± 0.13 | 10.46b ± 0.65 | 12.01a ± 1.75 |
| Protein and total sugar content (%) | 77.75c ± 0.15 | 80.05b ± 0.55 | 82.49b ± 0.99 | 83.06a ± 0.80 |
| Solubility (%) | 86.29c ± 0.88 | 90.63b ± 0.55 | 96.03a ± 0.67 | 94.78a ± 0.77 |
| Emulsifying activity index ($m^2/g$) | 6.21c ± 0.06 | 6.45b ± 0.05 | 7.08a ± 0.06 | 7.07a ± 0.08 |
| Emulsifying stability index (min) | 88.17c ± 5.95 | 104.05a ± 7.43 | 91.42c ± 1.63 | 98.45b ± 2.76 |
| Foaming capacity (%) | 58.89d ± 1.68 | 79.11c ± 2.69 | 98.44b ± 1.02 | 116.00a ± 1.33 |
| Foaming stability (%) | 20.03a ± 1.81 | 17.67a ± 2.19 | 10.39b ± 0.49 | 13.03b ± 0.22 |

It can be seen in Table 4 that ultrasonic treatment in step (4) significantly improves the extraction rate, the protein content, the protein and total sugar content, the solubility, the emulsifying activity index, the emulsifying stability index and the foaming capacity of sample 1-3-0. This is because ultrasonic wave increases the dissolution of the protein.

Embodiment 4 is an optimum embodiment. The extraction rate, the emulsifying activity index and the emulsifying stability index of the sample 1-2-1 prepared under this condition are increased by 32.10%, 8.46% and 309.74% respectively. In addition, the maximum total extraction rate of the flaxseed meal can reach 72.21% by two-step ultrasonic coupling, which is increased by 63.48% compared with the reference example.

The test item demonstrates that ultrasonic treatment can effectively change the substance composition and functional properties of the flaxseed protein-polysaccharide natural mixture (extracted in step 2) to achieve directional extraction in different application scenarios. Based on the improvement of the emulsifying activity index and the emulsifying stability index of the mixture by the test method, the low oil phase emulsion prepared by the component as an emulsifier is subsequently displayed, but the sample is not limited to the application scenario.

4. Test of Low Oil Phase Nanoemulsion in Embodiment 4

The low oil phase nanoemulsion prepared in step (5) of embodiment 4 was photographed. The results were shown in FIG. 4.

The average particle size and PDI (polymer dispersion index) were tested respectively. The results are shown in Table 5.

TABLE 5

Test Results of Low Oil Phase Nanoemulsion in Embodiment 4

| Emulsion Parameter | Value |
|---|---|
| Average particle size (nm) | 203.00 ± 4.40 |
| PDI | 0.17 ± 0.03 |

Figure 4:
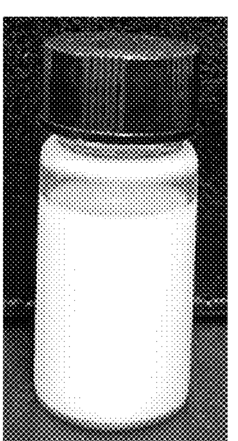
FIG. 4 shows low oil phase nanoemulsion prepared in step (5) of embodiment 4.

It can be seen in FIG. 4 and Table 5 that the average particle size of the obtained low oil phase nanoemulsion can reach about 200 nm and the PDI is only 0.17, which indicates that the component has a strong capability to stabilize the nanoemulsion. The oil phase of the emulsion is only 3%, but the emulsion shows a good emulsification effect and can be used for preparing complex plant milk and other products in the future.

5. Test of Flaxseed Protein-Polysaccharide Natural Mixtures I in Embodiment 2

The flaxseed protein-polysaccharide natural mixtures I prepared in step (2) of embodiments 10, 13 and 16 were recorded as sample 2-1, sample 2-2 and sample 2-3 respectively; and the sample without microwave treatment was used as control and recorded as sample 2-0. The extraction rate, protein content, total sugar content, protein and total sugar content, solubility, emulsifying activity index, emulsifying stability index, foaming capacity and foaming stability were tested respectively, and the results were shown in Table 6.

TABLE 6

| Test Results of Samples 2-0, 2-1, 2-2 and 2-3 | | | | |
|---|---|---|---|---|
| Test Item | Control Sample 2-0 | Embodiment 10 Sample 2-1 | Embodiment 13 Sample 2-2 | Embodiment 16 Sample 2-3 |
| Microwave power (W) in step (2) | 0 | 40 | 50 | 100 |
| Microwave time (min) in step (2) | 0 | 40 | 20 | 3 |
| Extraction rate (%) | 24.90c ± 1.23 | 31.20a ± 0.20 | 31.50a ± 0.15 | 29.55b ± 0.12 |
| Protein content (%) | 47.11bc ± 0.71 | 50.33a ± 0.79 | 47.99b ± 0.32 | 46.25c ± 0.84 |
| Total sugar content (%) | 38.23d ± 0.22 | 39.02c ± 0.33 | 47.49a ± 0.72 | 40.18b ± 0.25 |
| Protein and total sugar content (%) | 85.34c ± 0.69 | 89.36b ± 1.05 | 94.27a ± 0.89 | 88.55b ± 2.05 |
| Solubility (%) | 78.38b ± 0.56 | 84.99a ± 2.94 | 85.57a ± 0.78 | 85.70a ± 0.23 |
| Emulsifying activity index ($m^2/g$) | 7.30b ± 0.11 | 8.34a ± 0.09 | 8.48a ± 0.06 | 8.02b ± 0.11 |
| Emulsifying stability index (min) | 24.35c ± 1.76 | 28.39b ± 1.33 | 28.79b ± 0.89 | 35.89a ± 1.91 |
| Foaming capacity (%) | 99.44c ± 2.07 | 112.22b ± 4.15 | 135.00a ± 3.60 | 95.00c ± 3.60 |
| Foaming stability (%) | 25.59a ± 0.85 | 21.31b ± 0.93 | 24.68a ± 0.44 | 25.15a ± 0.21 |

It can be seen in Table 6 that low temperature microwave treatment in step (2) significantly improves the extraction rate, the total sugar content, the protein and total sugar content, the solubility, the emulsifying activity index, the emulsifying stability index and the foaming capacity of sample 2-0 (not significant for sample 2-3). Embodiment 13 is an optimum embodiment. The extraction rate and the foaming capacity of the sample 2-2 prepared under this condition are increased by 26.51% and 35.76% respectively. This is because the synergistic effect of the thermal effect and the non-thermal effect of microwaves destroys the cellular structure of flaxseed, reduces the viscosity of the extract and thus increases the dissolution of polysaccharide.

The test item demonstrates that low temperature microwave treatment can effectively change the substance composition and functional properties of the flaxseed protein-polysaccharide natural mixture (extracted in step 1) to achieve directional extraction in different application scenarios. Based on the improvement of the foaming capacity of the mixture by the test method, high-stability gel foam prepared by the component as a high efficiency foaming agent is subsequently displayed, but the sample is not limited to the application scenario.

6. Test of High-Stability Gel Foam in Embodiment 13

The high-stability gel foam prepared in step (3) of embodiment 13 was photographed. The results were shown in FIG. 5.

Figure 5:
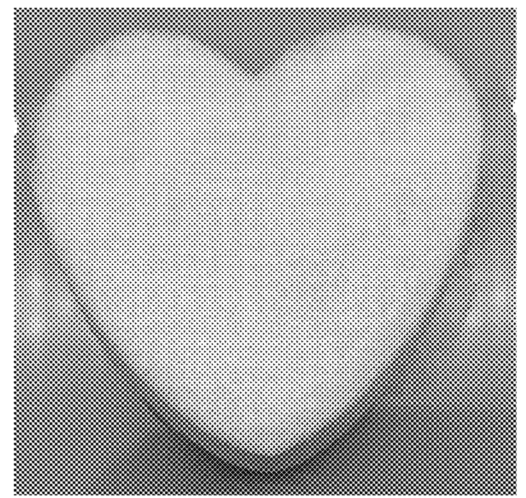
FIG. 5 shows high-stability gel foam prepared in step (3) of embodiment 13.

It can be seen in FIG. 5 that the high-stability gel foam prepared by the sample has good plasticity, and is delicate and uniform in porosity.

7. Test of Flaxseed Protein-Polysaccharide Natural Mixtures II in Embodiments 10-18

The flaxseed protein-polysaccharide natural mixtures II prepared in step (4) of embodiments 10-18 were recorded as sample 2-1-1, sample 2-1-2, sample 2-1-3, sample 2-2-1, sample 2-2-2, sample 2-2-3, sample 2-3-1, sample 2-3-2 and sample 2-3-3 respectively; and the samples without ultrasonic treatment were used as control and recorded as sample 2-1-0, sample 2-2-0 and sample 2-3-0 respectively. The extraction rate, protein content, total sugar content, protein and total sugar content, solubility, emulsifying activity index, emulsifying stability index, foaming capacity and foaming stability were tested respectively, and the results were shown in Tables 7-9.

TABLE 7

| Test Results of Samples 2-1-0, 2-1-1, 2-1-2 and 2-1-3 | | | | |
|---|---|---|---|---|
| Test Item | Control Sample 2-1-0 | Embodiment 10 Sample 2-1-1 | Embodiment 11 Sample 2-1-2 | Embodiment 12 Sample 2-1-3 |
| Microwave power (W) in step (2) | 40 | | | |
| Microwave time (min) in step (2) | 40 | | | |
| Ultrasonic power (W/mL) in step (4) | 0 | 1 | 10 | 20 |
| Ultrasonic time (min) in step (4) | 0 | 60 | 30 | 10 |
| Extraction rate (%) | 16.25d ± 0.72 | 25.12b ± 0.11 | 26.84a ± 0.49 | 22.93c ± 0.53 |
| Protein content (%) | 63.28c ± 0.08 | 65.11b ± 0.01 | 67.81a ± 0.40 | 64.80b ± 0.08 |
| Total sugar content (%) | 20.32d ± 0.04 | 24.83a ± 0.04 | 22.64c ± 0.09 | 24.19b ± 0.15 |
| Protein and total sugar content (%) | 83.60c ± 0.14 | 89.93ab ± 0.04 | 90.45a ± 0.56 | 88.98b ± 0.91 |
| Solubility (%) | 94.46a ± 1.73 | 94.90a ± 0.91 | 93.76a ± 1.06 | 94.75a ± 2.57 |
| Emulsifying | 7.60a ± 0.06 | 7.20b ± 0.03 | 6.63c ± 0.10 | 5.80d ± 0.05 |

TABLE 7-continued

Test Results of Samples 2-1-0, 2-1-1, 2-1-2 and 2-1-3

| Test Item | Control Sample 2-1-0 | Embodiment 10 Sample 2-1-1 | Embodiment 11 Sample 2-1-2 | Embodiment 12 Sample 2-1-3 |
|---|---|---|---|---|
| activity index ($m^2/g$) | | | | |
| Emulsifying stability index (min) | 66.39c ± 4.05 | 71.49c ± 5.13 | 251.25a ± 10.35 | 154.20b ± 17.17 |
| Foaming capacity (%) | 58.33d ± 4.41 | 96.11b ± 3.47 | 107.22a ± 4.19 | 84.44c ± 1.92 |
| Foaming stability (%) | 28.40a ± 3.76 | 13.85b ± 0.92 | 2.70c ± 0.72 | 3.95c ± 1.60 |

It can be seen in Table 7 that ultrasonic treatment in step (4) significantly improves the extraction rate, the protein content, the total sugar content, the protein and total sugar content, the emulsifying stability index and the foaming capacity of sample 2-1-0. This is because ultrasonic wave increases the dissolution of the protein and the polysaccharide.

TABLE 8

Test Results of Samples 2-2-0, 2-2-1, 2-2-2 and 2-2-3

| Test Item | Control Sample 2-2-0 | Embodiment 13 Sample 2-2-1 | Embodiment 14 Sample 2-2-2 | Embodiment 15 Sample 2-2-3 |
|---|---|---|---|---|
| Microwave power (W) in step (2) | | | 50 | |
| Microwave time (min) in step (2) | | | 20 | |
| Ultrasonic power (W/mL) in step (4) | 0 | 1 | 10 | 20 |
| Ultrasonic time (min) in step (4) | 0 | 60 | 30 | 10 |
| Extraction rate (%) | 17.22b ± 0.05 | 26.21a ± 1.01 | 30.15a ± 1.89 | 27.96a ± 0.93 |
| Protein content (%) | 63.33c ± 0.18 | 64.81b ± 0.16 | 65.27a ± 0.13 | 64.68b ± 0.08 |
| Total sugar content (%) | 18.18b ± 0.64 | 22.98a ± 0.49 | 24.73a ± 1.41 | 22.93a ± 0.30 |
| Protein and total sugar content (%) | 81.52c ± 0.49 | 87.79b ± 0.64 | 89.99a ± 1.51 | 87.61b ± 0.29 |
| Solubility (%) | 95.98a ± 1.98 | 94.78a ± 1.61 | 95.00a ± 1.78 | 94.29a ± 2.00 |
| Emulsifying activity index ($m^2/g$) | 8.06a ± 0.14 | 7.34b ± 0.16 | 6.91c ± 0.04 | 6.76c ± 0.11 |
| Emulsifying stability index (min) | 103.41c ± 2.46 | 172.52b ± 25.92 | 270.48a ± 26.02 | 216.34ab ± 34.02 |
| Foaming capacity (%) | 50.56c ± 2.08 | 82.78b ± 2.83 | 116.11a ± 2.08 | 78.89b ± 4.16 |
| Foaming stability (%) | 26.49a ± 6.00 | 7.32c ± 2.30 | 14.80b ± 2.25 | 2.08d ± 2.94 |

It can be seen in Table 8 that ultrasonic treatment in step (4) significantly improves the extraction rate, the protein content, the total sugar content, the protein and total sugar content, the emulsifying stability index and the foaming capacity of sample 2-2-0. This is because ultrasonic wave improved the dissolution of the protein and the polysaccharide.

TABLE 9

| Test Results of Samples 2-3-0, 2-3-1, 2-3-2 and 2-3-3 | | | | |
|---|---|---|---|---|
| Test Item | Control Sample 2-3-0 | Embodiment 16 Sample 2-3-1 | Embodiment 17 Sample 2-3-2 | Embodiment 18 Sample 2-3-3 |
| Microwave power (W) in step (2) | 100 | | | |
| Microwave time (min) in step (2) | 3 | | | |
| Ultrasonic power (W/mL) in step (4) | 0 | 1 | 10 | 20 |
| Ultrasonic time (min) in step (4) | 0 | 60 | 30 | 10 |
| Extraction rate (%) | 14.58c ± 1.08 | 24.92b ± 0.40 | 28.76a ± 0.37 | 25.19b ± 1.47 |
| Protein content (%) | 65.91c ± 0.58 | 66.91b ± 0.22 | 68.23a ± 0.18 | 64.86d ± 0.11 |
| Total sugar content (%) | 16.36d ± 0.04 | 19.56b ± 0.26 | 18.99c ± 0.41 | 20.37a ± 0.22 |
| Protein and total sugar content (%) | 82.27c ± 0.69 | 86.47a ± 0.44 | 87.22a ± 0.18 | 85.24b ± 0.34 |
| Solubility (%) | 95.17a ± 1.50 | 94.62a ± 1.17 | 94.89a ± 1.14 | 94.44a ± 2.09 |
| Emulsifying activity index ($m^2/g$) | 8.27a ± 0.08 | 6.82c ± 0.07 | 7.09b ± 0.05 | 6.74c ± 0.08 |
| Emulsifying stability index (min) | 102.20c ± 4.37 | 192.14a ± 11.87 | 136.56b ± 17.56 | 129.26d ± 4.71 |
| Foaming capacity (%) | 57.78c ± 3.85 | 113.33b ± 3.33 | 136.67a ± 3.33 | 113.56b ± 1.68 |
| Foaming stability (%) | 26.85a ± 1.60 | 8.32c ± 2.16 | 1.29d ± 1.23 | 11.64b ± 1.26 |

It can be seen in Table 9 that ultrasonic treatment in step (4) significantly improves the extraction rate, the protein content, the total sugar content, the protein and total sugar content, the emulsifying stability index and the foaming capacity of sample 3-3-0. This is because ultrasonic wave increases the dissolution of the protein and the polysaccharide.

Embodiment 14 is an optimum embodiment. The extraction rate and the emulsifying stability index of the sample 2-2-2 prepared under this condition are 75.09% and 161.56% respectively. In addition, the maximum total extraction rate of the flaxseed meal can reach 61.65% by microwave and ultrasonic coupling, which is increased by 46.37% compared with the reference example.

The test item demonstrates that ultrasonic treatment can effectively change the substance composition and functional properties of the flaxseed protein-polysaccharide natural mixture (extracted in step 2) to achieve directional extraction in different application scenarios. Based on the improvement of the emulsifying activity index and the emulsifying stability index by the test method, the foamed emulsion prepared by the component as an emulsifier is subsequently displayed, but the sample is not limited to the application scenario.

8. Test of Foamed Emulsion in Embodiment 14

The foamed emulsion prepared in step (5) of embodiment 14 was shaped and then photographed. The overflowed rate was represented by the volumes of the foamed emulsion and the emulsion before whipping. The results were shown in FIG. 6.

Figure 6:
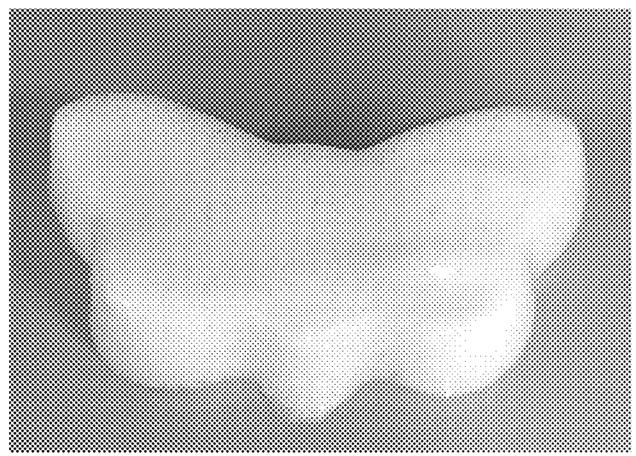
FIG. 6 Shows foamed emulsion prepared in step (5) of embodiment 14.

It can be seen in FIG. 6 that the component has good emulsifying stability index, and can stabilize coconut oil with 10% oil phase. When combined with sample 2-2, the foamed emulsion can be obtained, and the foaming rate reaches 309%. The foamed emulsion can be used for preparing plant-based ice cream or plant-based cakes in the future.

9. Test of Flaxseed Protein-Polysaccharide Natural Mixtures I in Embodiments 19, 22 And 25

The flaxseed protein-polysaccharide natural mixtures I prepared in step (2) of embodiments 19, 22 and 25 were recorded as sample 3-1, sample 3-2 and sample 3-3 respectively; and the sample without bio-enzyme treatment was used as control and recorded as sample 3-0. The extraction rate, protein content, total sugar content, protein and total sugar content, solubility, emulsifying activity index, emulsifying stability index, foaming capacity and foaming stability were tested respectively, and the results were shown in Table 10.

TABLE 10

| Test Results of Samples 3-0, 3-1, 3-2 and 3-3 | | | | |
|---|---|---|---|---|
| Test Item | Control Sample 3-0 | Embodiment 19 Sample 3-1 | Embodiment 22 Sample 3-2 | Embodiment 25 Sample 3-3 |
| Bio-enzyme type in step (2) | None | Pectase | Cellulase | Hemicellulase |
| Extraction rate (%) | 26.87d ± 1.89 | 46.87a ± 0.98 | 31.30c ± 0.29 | 38.84b ± 0.68 |

TABLE 10-continued

Test Results of Samples 3-0, 3-1, 3-2 and 3-3

| Test Item | Control Sample 3-0 | Embodiment 19 Sample 3-1 | Embodiment 22 Sample 3-2 | Embodiment 25 Sample 3-3 |
|---|---|---|---|---|
| Protein content (%) | 48.39a ± 1.17 | 36.81d ± 1.06 | 44.27b ± 0.36 | 40.67c ± 0.48 |
| Total sugar content (%) | 35.77d ± 0.21 | 42.98b ± 0.64 | 39.54c ± 0.13 | 45.59a ± 0.72 |
| Protein and total sugar content (%) | 84.17ab ± 1.14 | 79.80c ± 1.57 | 83.81ab ± 0.35 | 86.26a ± 1.20 |
| Solubility (%) | 79.41c ± 1.40 | 94.92a ± 0.57 | 92.85b ± 0.64 | 91.94b ± 1.31 |
| Emulsifying activity index ($m^2/g$) | 7.20d ± 0.11 | 7.93b ± 0.25 | 7.97b ± 0.16 | 8.23a ± 0.17 |
| Emulsifying stability index (min) | 25.88c ± 0.31 | 84.73c ± 0.08 | 87.20b ± 9.84 | 178.89a ± 19.22 |
| Foaming capacity (%) | 101.56a ± 1.37 | 93.78b ± 2.79 | 95.11b ± 1.37 | 37.78c ± 0.83 |
| Foaming stability (%) | 26.04a ± 0.48 | 16.76c ± 0.68 | 26.21a ± 0.36 | 23.49b ± 1.84 |

It can be seen in Table 10 that different bio-enzyme treatment significantly improves the extraction rate, the total sugar content, the solubility, the emulsifying activity index and the emulsifying stability index of sample 3-0. This is because enzymolysis damages the cell structure of flaxseed or conducts enzymatic hydrolysis for macromolecules to form micromolecules, thus reduces the viscosity of the extract and increases the dissolution of polysaccharide.

Embodiment 19 is an optimum embodiment. The extraction rate and the solubility of the sample 3-1 prepared under this condition are increased by 74.43% and 19.53% respectively.

The test item demonstrates that the addition of the bio-enzyme can effectively change the substance composition and functional properties of the flaxseed protein-polysaccharide natural mixture (extracted in step 1) to achieve directional extraction in different application scenarios. Based on the improvement of the solubility of the mixture by the test method, the low-turbidity solution of the component is subsequently displayed, and can be added to low-turbidity plant protein drinks in the future, but the sample is not limited to the application scenario.

10. Test of Low-Turbidity Plant Protein Drinks in Embodiments 19, 22 and 25

The use amounts of the flaxseed protein-polysaccharide natural mixtures I prepared in step (3) of embodiments 19, 22 and 25 were changed, and solutions with mass percent of 0.1%, 0.5%, 1%, 1.5% and 2% were prepared respectively and photographed. The results were shown in FIG. 7.

Figure 7:
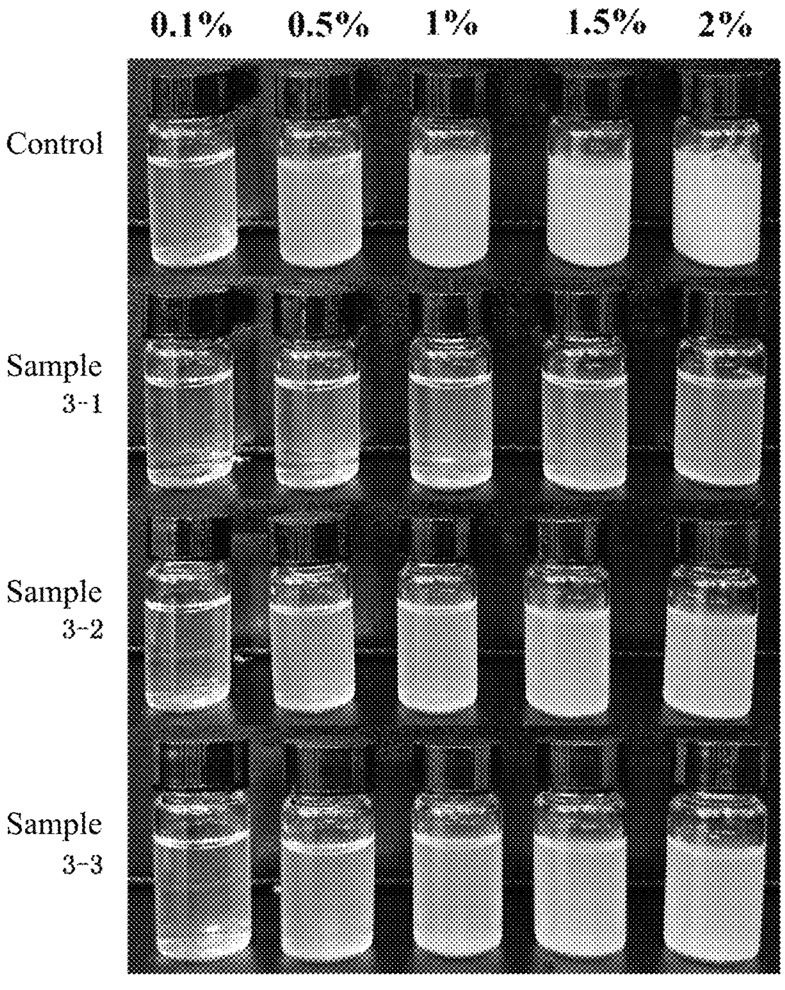
FIG. 7 shows a low-turbidity plant protein drink prepared in step (3) of embodiment 19.

It can be seen in FIG. 7 that bio-enzyme treatment greatly reduces the turbidity of the product solution, wherein pectase has the best effect. Samples treated with different bio-enzymes can be added as a nutritional supplement to the low-turbidity plant protein drinks. In addition, because oligosaccharide is produced by enzymolysis, this additive component may also have certain biological activity.

11. Test of Flaxseed Protein-Polysaccharide Natural Mixtures II in Embodiments 19-27

The flaxseed protein-polysaccharide natural mixtures II prepared in step (4) of embodiments 19-27 were recorded as sample 3-1-1, sample 3-1-2, sample 3-1-3, sample 3-2-1, sample 3-2-2, sample 3-2-3, sample 3-3-1, sample 3-3-2 and sample 3-3-3 respectively; and the samples without ultrasonic treatment were used as control and recorded as sample 3-1-0, sample 3-2-0 and sample 3-3-0 respectively. The extraction rate, protein content, total sugar content, protein and total sugar content, solubility, emulsifying activity index, emulsifying stability index, foaming capacity and foaming stability are tested respectively, and the results were shown in Tables 11-13.

TABLE 11

Test Results of Samples 3-1-0, 3-1-1, 3-1-2 and 3-1-3

| Test Item | Control Sample 3-1-0 | Embodiment 19 Sample 3-1-1 | Embodiment 20 Sample 3-1-2 | Embodiment 21 Sample 3-1-3 |
|---|---|---|---|---|
| Bio-enzyme type in step (2) | Pectase | | | |
| Ultrasonic power (W/mL) in step (4) | 0 | 1 | 10 | 20 |
| Ultrasonic time (min) in step (4) | 0 | 60 | 30 | 10 |
| Extraction rate (%) | 17.98c ± 0.18 | 18.81b ± 0.09 | 18.87b ± 0.21 | 19.61a ± 0.30 |
| Protein content (%) | 50.36c ± 0.35 | 52.53b ± 0.34 | 54.28a ± 0.08 | 50.11c ± 0.39 |
| Total sugar content (%) | 18.65d ± 0.09 | 24.36a ± 0.38 | 20.18c ± 0.15 | 20.94b ± 0.28 |
| Protein and total sugar content (%) | 69.01d ± 0.44 | 76.89a ± 0.71 | 74.46b ± 0.21 | 71.05c ± 0.63 |

TABLE 11-continued

| Test Results of Samples 3-1-0, 3-1-1, 3-1-2 and 3-1-3 | | | | |
|---|---|---|---|---|
| Test Item | Control Sample 3-1-0 | Embodiment 19 Sample 3-1-1 | Embodiment 20 Sample 3-1-2 | Embodiment 21 Sample 3-1-3 |
| Solubility (%) | 93.90b ± 0.61 | 95.01a ± 0.98 | 95.30a ± 1.45 | 93.96b ± 0.36 |
| Emulsifying activity index ($m^2/g$) | 7.49c ± 0.05 | 10.38a ± 0.22 | 7.66b ± 0.04 | 7.65b ± 0.04 |
| Emulsifying stability index (min) | 78.53a ± 8.36 | 19.68b ± 1.98 | 20.50b ± 3.32 | 22.83b ± 1.32 |
| Foaming capacity (%) | 61.11a ± 5.57 | 35.56b ± 4.63 | 38.00b ± 4.46 | 58.89a ± 5.57 |
| Foaming stability (%) | 25.06c ± 4.59 | 45.87b ± 5.20 | 41.11b ± 3.19 | 65.67a ± 3.32 |

It can be seen in Table 11 that ultrasonic treatment in step (4) significantly improves the extraction rate, the protein content (not significant for sample 3-1-3), the total sugar content, the protein and total sugar content, the solubility, the emulsifying activity index and the foaming stability of sample 3-1-0. This is because ultrasonic wave increases the dissolution of the polysaccharide.

TABLE 12

| Test Results of Samples 3-2-0, 3-2-1, 3-2-2 and 3-2-3 | | | | |
|---|---|---|---|---|
| Test Item | Control Sample 3-2-0 | Embodiment 22 Sample 3-2-1 | Embodiment 23 Sample 3-2-2 | Embodiment 24 Sample 3-2-3 |
| Bio-enzyme type in step (2) | Cellulase | | | |
| Ultrasonic power (W/mL) in step (4) | 0 | 1 | 10 | 20 |
| Ultrasonic time (min) in step (4) | 0 | 60 | 30 | 10 |
| Extraction rate (%) | 19.31c ± 0.19 | 22.47b ± 0.73 | 23.41a ± 0.42 | 19.71c ± 0.21 |
| Protein content (%) | 56.48b ± 0.15 | 58.17a ± 0.39 | 53.32c ± 0.44 | 49.44d ± 0.83 |
| Total sugar content (%) | 22.24c ± 0.42 | 26.52a ± 0.07 | 25.07b ± 0.15 | 26.38a ± 0.13 |
| Protein and total sugar content (%) | 78.72b ± 0.33 | 84.69a ± 0.32 | 78.39b ± 0.55 | 75.82c ± 0.90 |
| Solubility (%) | 96.46c ± 1.06 | 97.83b ± 0.83 | 98.49a ± 0.58 | 97.40b ± 0.62 |
| Emulsifying activity index ($m^2/g$) | 5.91c ± 0.08 | 6.34b ± 0.11 | 6.52b ± 0.07 | 6.93a ± 0.07 |
| Emulsifying stability index (min) | 86.94c ± 4.73 | 147.53a ± 19.79 | 128.01b ± 2.06 | 140.83a ± 10.07 |
| Foaming capacity (%) | 53.78b ± 7.39 | 49.56b ± 3.00 | 63.56a ± 6.36 | 58.67ab ± 3.81 |
| Foaming stability (%) | 27.36a ± 4.26 | 15.49b ± 1.84 | 16.93b ± 0.62 | 18.33b ± 2.35 |

It can be seen in Table 12 that ultrasonic treatment in step (4) significantly improves the extraction rate (not significant for sample 3-2-3), the total sugar content, the protein and total sugar content (not significant for sample 3-2-2 and sample 3-2-3), the solubility, the emulsifying activity index and the emulsifying stability index of sample 3-2-0. This is because ultrasonic wave increases the dissolution of the polysaccharide.

TABLE 13

| Test Results of Samples 3-3-0, 3-3-1, 3-3-2 and 3-3-3 | | | | |
|---|---|---|---|---|
| Test Item | Control Sample 3-3-0 | Embodiment 25 Sample 3-3-1 | Embodiment 26 Sample 3-3-2 | Embodiment 27 Sample 3-3-3 |
| Bio-enzyme type in step (2) | Hemicellulase | | | |

TABLE 13-continued

Test Results of Samples 3-3-0, 3-3-1, 3-3-2 and 3-3-3

| Test Item | Control Sample 3-3-0 | Embodiment 25 Sample 3-3-1 | Embodiment 26 Sample 3-3-2 | Embodiment 27 Sample 3-3-3 |
|---|---|---|---|---|
| Ultrasonic power (W/mL) in step (4) | 0 | 1 | 10 | 20 |
| Ultrasonic time (min) in step (4) | 0 | 60 | 30 | 10 |
| Extraction rate (%) | 16.69c ± 0.30 | 19.21a ± 0.31 | 18.22b ± 0.81 | 18.86b ± 0.30 |
| Protein content (%) | 47.23a ± 0.64 | 48.68a ± 0.70 | 44.04c ± 0.99 | 46.43b ± 0.38 |
| Total sugar content (%) | 21.21d ± 0.39 | 32.38a ± 0.43 | 26.18b ± 0.18 | 25.10c ± 0.30 |
| Protein and total sugar content (%) | 68.44c ± 1.03 | 81.06a ± 0.87 | 70.22b ± 0.99 | 71.52b ± 0.54 |
| Solubility (%) | 94.04a ± 0.56 | 93.63a ± 0.12 | 93.38a ± 0.25 | 94.83a ± 1.04 |
| Emulsifying activity index ($m^2$/g) | 8.38c ± 0.06 | 8.40c ± 0.29 | 10.21b ± 0.15 | 9.79a ± 0.06 |
| Emulsifying stability index (min) | 33.39a ± 3.01 | 30.54a ± 2.67 | 15.99b ± 0.24 | 24.87b ± 0.35 |
| Foaming capacity (%) | 111.11a ± 4.16 | 81.11b ± 5.67 | 86.22b ± 5.48 | 85.11b ± 4.76 |
| Foaming stability (%) | 35.27b ± 9.36 | 58.55a ± 3.41 | 42.30b ± 3.68 | 40.75b ± 3.03 |

It can be seen in Table 13 that ultrasonic treatment in step (4) significantly improves the extraction rate, the total sugar content, the protein and total sugar content, the solubility, the emulsifying activity index (not significant for sample 3-3-1) and the foaming stability of sample 3-3-0. This is because ultrasonic wave increases the dissolution of the polysaccharide.

Embodiment 22 is an optimum embodiment. The extraction rate, the solubility and the total amount of the protein and the polysaccharide of the sample 3-2-1 prepared under this condition are increased by 16.36%, 1.42% and 0.76% respectively. In addition, the maximum total extraction rate of the flaxseed meal can reach 70.28% by bio-enzyme-ultrasonic coupling, which is increased by 52.19% compared with the reference example.

The test item demonstrates that ultrasonic treatment can effectively change the substance composition and functional properties of the flaxseed protein-polysaccharide natural mixture (extracted in step 2) to achieve directional extraction in different application scenarios. Based on the improvement of the solubility and the nutritional ingredient of the mixture by the test method, the component as a nutritional supplement is added to the meal replacement milkshake, but the sample is not limited to the application scenario.

12. Test of Meal Replacement Milkshake in Embodiment 22

The meal replacement milkshake prepared in step (5) of embodiment 22 was photographed. The results were shown in FIG. 8.

Figure 8:
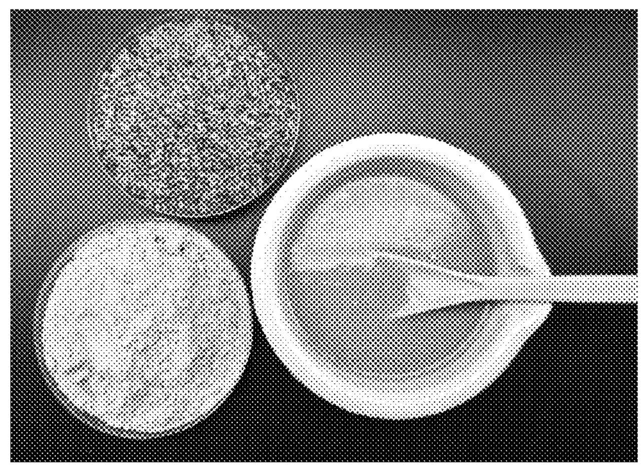
FIG. 8 shows meal replacement milkshake prepared in step (5) of embodiment 22.

It can be seen in FIG. 8 that the meal replacement milkshake has no obvious caking, and has good flowability.

Physical and chemical properties were tested, and the results were shown in Table 14.

TABLE 14

Test Results of Meal Replacement Milkshake in Embodiment 22

| Physical and Chemical Properties | Value |
|---|---|
| Dispersibility/s | 84.58 ± 1.27 |
| Wettability/s | 76.7 ± 7.39 |

It can be seen in Table 14 that the wettability and the dispersibility of the meal replacement milkshake are good.

13. Test of Flaxseed Protein-Polysaccharide Natural Mixtures I and II in Reference Example The flaxseed protein-polysaccharide natural mixture I prepared in step (2) and the flaxseed protein-polysaccharide natural mixture II prepared in step (3) in the reference example were taken, and the extraction rate, protein content, total sugar content, protein and total sugar content, solubility, emulsifying activity index, emulsifying stability index, foaming capacity and foaming stability were tested respectively. The results were shown in Table 15.

TABLE 15

Test Results of Flaxseed Protein-Polysaccharide Natural mixtures I and II in Reference Example

| Test Item | Flaxseed Protein-Polysaccharide Natural mixture I | Flaxseed Protein-Polysaccharide Natural mixture II |
|---|---|---|
| Extraction rate (%) | 24.48 ± 0.52 | 20.10 ± 0.16 |
| Protein content (%) | 44.23 ± 1.14 | 59.84 ± 0.44 |
| Total sugar content (%) | 36.54 ± 0.25 | 21.24 ± 0.72 |
| Protein and total sugar content (%) | 80.78 ± 1.34 | 81.08 ± 0.28 |
| Solubility (%) | 78.82 ± 0.62 | 77.27 ± 1.21 |
| Emulsifying activity index ($m^2$/g) | 7.22 ± 0.07 | 7.97 ± 0.05 |
| Emulsifying stability index (min) | 24.33 ± 0.63 | 20.21 ± 0.26 |
| Foaming capacity (%) | 96.89 ± 2.74 | 52.33 ± 2.33 |
| Foaming stability (%) | 26.56 ± 0.60 | 47.72 ± 1.06 |

It can be seen in Table 15 that the total extraction rate of the flaxseed meal is only 44.58% by two-step extraction in the reference example.

The above contrast tests indicate that compared with the traditional extraction mode of the flaxseed protein, the method of the present invention can extract active components from the flaxseed meal more efficiently, greenly and moderately, solves the problem of low extraction rate of the flaxseed protein-polysaccharide natural mixture from water extraction, can obtain flaxseed protein-polysaccharide natural mixtures of different proportions and properties, enriches the orientability of the extraction process and can realize the multi-scenario utilization of different components.

The above description of the disclosed embodiments enables those skilled in the art to realize or use the present invention. Many modifications to these embodiments will be apparent to those skilled in the art. The general principle defined herein can be realized in other embodiments without departing from the spirit or scope of the present invention. Therefore, the present invention will not be limited to these embodiments shown herein, but will conform to the widest scope consistent with the principle and novel features disclosed herein.

What is claimed is:

1. A method for extraction and multi-scenario utilization of a flaxseed protein-polysaccharide natural mixture, specifically comprising the following steps:

(1) raw material pretreatment firstly crushing, sieving and degreasing flaxseed meal to obtain flaxseed degreased meal powder; and then dissolving the flaxseed degreased meal powder in water and stirring to obtain flaxseed degreased meal powder rinsing solution;

(2) extraction of flaxseed protein-polysaccharide natural mixture I firstly conducting ultrasonic treatment for the flaxseed degreased meal powder rinsing solution, or firstly conducting microwave treatment for the flaxseed degreased meal powder rinsing solution, or firstly adding a bio-enzyme into the flaxseed degreased meal powder rinsing solution and stirring in a water bath, wherein the bio-enzyme is pectase, cellulase or hemicellulase; then centrifuging, taking supernatant and freeze-drying to obtain the flaxseed protein-polysaccharide natural mixture I;

(3) utilization of the flaxseed protein-polysaccharide natural mixture I firstly, dissolving the flaxseed protein-polysaccharide natural mixture I prepared by ultrasonic treatment in the step (2), gum Arabic and maltodextrin in water and hydrating overnight; then adding oil containing n-3 polyunsaturated fatty acid, shearing, introducing a high-pressure microfluidization, adding food grade silica powder and shaking up to obtain emulsion containing n-3 polyunsaturated fatty acid; and finally, spray-drying the emulsion to obtain powdered oil containing n-3 polyunsaturated fatty acid, wherein a pressure of the high-pressure microfluidization is 750 bar;

or, firstly dissolving the flaxseed protein-polysaccharide natural mixture I prepared by microwave treatment in the step (2) in water and adjusting pH to acidity; then heating in a water bath and whipping; and finally, treating in an ice bath to room temperature to obtain gel foam;

or, using the flaxseed protein-polysaccharide natural mixture I prepared by the bio-enzyme in the step (2) as a protein ingredient for preparing a low-turbidity plant protein drink;

(4) extraction of flaxseed protein-polysaccharide natural mixture II firstly, redissolving a precipitate obtained after centrifugation in the step (2) to same volume as the flaxseed degreased meal powder rinsing solution to obtain a redissolution solution, adjusting pH of the redissolution solution to alkalinity and conducting magnetic stirring to obtain an alkali extraction solution of the flaxseed degreased meal powder; then, conducting ultrasonic treatment for the alkali extraction solution of the flaxseed degreased meal powder, centrifuging, taking supernatant and freeze-drying to obtain the flaxseed protein-polysaccharide natural mixture II;

(5) utilization of the flaxseed protein-polysaccharide natural mixture II firstly dissolving the flaxseed protein-polysaccharide natural mixture II in water, then adding the oil containing n-3 polyunsaturated fatty acid, and after shearing, introducing a high-pressure microfluidization to obtain low oil phase nanoemulsion, wherein a pressure of the high-pressure microfluidization is 500 bar;

or, firstly dissolving the flaxseed protein-polysaccharide natural mixture II and sucrose in water, adding coconut oil, shearing to obtain macroemulsion, introducing the high-pressure microfluidization to obtain miniemulsion, then adding the flaxseed protein-polysaccharide natural mixture I prepared by microwave treatment in the step (2) for magnetic stirring, aging, adjusting pH to acidity, and whipping in an ice bath to obtain foamed emulsion;

or, mixing and crushing the flaxseed protein-polysaccharide natural mixture II, pea protein isolate, hemp seed protein, soybean protein isolate, perilla protein, perilla peptide, microcapsule powder containing n-3 polyunsaturated fatty acid, medium chain triglycerides microcapsule powder, psyllium husk powder, maltodextrin, oat flour, flaxseed powder, resistant dextrin, chitosan oligosaccharide, yacon, inulin, fructo oligosaccharide, erythritol, konjaku flour and stevioside to obtain a meal replacement milkshake.

2. The method for extraction and multi-scenario utilization of the flaxseed protein-polysaccharide natural mixture according to claim 1, wherein in the step (1), mesh number of a sieve for the sieving is 60 meshes; the volume ratio of the flaxseed degreased meal powder to the water is 1:15; and the rotational speed of the stirring is 1600 rpm, temperature is 40° C. and time is 3 h.

3. The method for extraction and multi-scenario utilization of the flaxseed protein-polysaccharide natural mixture according to claim 1, wherein in the step (2), power of the ultrasonic treatment is 1-20 W/mL and time is 10-60 min; the temperature of the microwave treatment is 60° C., power is 40-100 W and time is 3-40 min; the mass-to-volume ratio of the bio-enzyme to the flaxseed degreased meal powder rinsing solution is 1 g:100 mL; a temperature of the stirring in the water bath is 50° C., and time is 2 h; and the temperature of the centrifuging is 20° C., rotational speed is 10000 rpm and time is 30 min.

4. The method for extraction and multi-scenario utilization of the flaxseed protein-polysaccharide natural mixture according to claim 1, wherein in the step (3), in a preparation process of the powdered oil, a mass-to-volume ratio of the flaxseed protein-polysaccharide natural mixture I, the gum Arabic, the maltodextrin, the water, the oil containing n-3 polyunsaturated fatty acid and the food grade silica powder is 2.5 g:2.5 g:5 g:100 mL:2.5 g:0.3 g; a temperature of hydrating overnight is 4° C.; a shear rate is 15000 rpm and time is 10 min; cycle times of the high-pressure microfluidization is 3; an air inlet temperature of the spray-drying is 160° C., and a feed rate is 7 mL/min.

5. The method for extraction and multi-scenario utilization of the flaxseed protein-polysaccharide natural mixture according to claim 1, wherein in the step (3), in a preparation process of the foam, a mass-to-volume ratio of the flaxseed protein-polysaccharide natural mixture I to the water is 2 g:50 mL; the pH is adjusted to 3.5; a temperature of the heating in the water bath is 50° C. and time is 10 min; the time of the whipping is 5 min.

6. The method for extraction and multi-scenario utilization of the flaxseed protein-polysaccharide natural mixture according to claim 1, wherein in the step (4), the pH is adjusted to 9.0; time of the magnetic stirring is 2 h; power of the ultrasonic treatment is 1-20 W/mL and time is 10-60 min; and a temperature of the centrifuging is 4° C., rotational speed is 10000 rpm and time is 30 min.

7. The method for extraction and multi-scenario utilization of the flaxseed protein-polysaccharide natural mixture according to claim 1, wherein in the step (5), in a preparation process of the low oil phase nanoemulsion, a mass-to-volume ratio of the flaxseed protein-polysaccharide natural mixture II, the water and the oil containing n-3 polyunsaturated fatty acid is 1.5 g:100 mL:3 g; a shear rate is 15000 rpm and time is 5 min; and cycle times of the high-pressure microfluidization is 3.

8. The method for extraction and multi-scenario utilization of the flaxseed protein-polysaccharide natural mixture according to claim 1, wherein in the step (5), in a preparation process of the foamed emulsion, a mass-to-volume ratio of the flaxseed protein-polysaccharide natural mixture II, the sucrose, the water, the coconut oil and the flaxseed protein-polysaccharide natural mixture I is 2 g:15 g:90 mL:10 mL:2 g; a temperature of the coconut oil is 60° C.; a shear rate is 15000 rpm and time is 5 min; cycle times of the high-pressure microfluidization is 2; time of the magnetic stirring is 6 h; a temperature of the aging is 4° C., and time is 6 h; the pH is adjusted to 4.0; and time of the whipping is 20 min.

9. The method for extraction and multi-scenario utilization of the flaxseed protein-polysaccharide natural mixture according to claim 1, wherein in the step (5), in a preparation process of the meal replacement milkshake, weight parts of raw materials are: 2 parts of the flaxseed protein-polysaccharide natural mixture II, 9 parts of the pea protein isolate, 3 parts of the hemp seed protein, 7 parts of the soybean protein isolate, 5 parts of the perilla protein, 3 parts of the perilla peptide, 5 parts of the microcapsule powder containing n-3 polyunsaturated fatty acid, 3 parts of the medium chain triglycerides microcapsule powder, 2 parts of the psyllium husk powder, 6 parts of the maltodextrin, 1 part of the oat flour, 1 part of the flaxseed powder, 5 parts of the resistant dextrin, 0.1 part of the chitosan oligosaccharide, 0.5 part of the yacon, 1 part of the inulin, 1 part of the fructo oligosaccharide, 1 part of the erythritol, 2 parts of the konjaku flour and 0.04 part of the stevioside.

* * * * *